US008685694B2

(12) United States Patent
Rao

(10) Patent No.: US 8,685,694 B2
(45) Date of Patent: Apr. 1, 2014

(54) METHODS AND COMPOSITIONS COMPRISING BACTERIOPHAGE NANOPARTICLES

(75) Inventor: Venigalla Basaveswara Rao, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 590 days.

(21) Appl. No.: 11/015,294

(22) Filed: Dec. 17, 2004

(65) Prior Publication Data

US 2005/0226892 A1 Oct. 13, 2005

Related U.S. Application Data

(60) Provisional application No. 60/530,527, filed on Dec. 17, 2003.

(51) Int. Cl.
| | | |
|---|---|---|
| C12N 15/85 | (2006.01) | |
| C12N 15/86 | (2006.01) | |
| C12Q 1/68 | (2006.01) | |
| C12Q 1/70 | (2006.01) | |
| A61K 48/00 | (2006.01) | |
| C12N 7/00 | (2006.01) | |
| C07K 14/005 | (2006.01) | |
| A61K 39/295 | (2006.01) | |
| C12N 15/10 | (2006.01) | |
| A61K 39/00 | (2006.01) | |

(52) U.S. Cl.
CPC .............. *C12N 7/00* (2013.01); *C12N 15/1037* (2013.01); *C07K 14/005* (2013.01); *C07K 2319/735* (2013.01); *C07K 2319/00* (2013.01); *C07K 2299/00* (2013.01); *A61K 2039/6075* (2013.01); *A61K 2039/64* (2013.01); *A61K 2039/645* (2013.01); *A61K 39/295* (2013.01)
USPC ............... 435/235.1; 424/184.1; 424/199.1; 424/93.1; 435/456; 435/5

(58) Field of Classification Search
USPC ................... 435/5, 69.1, 471, 235.1, 456; 424/184.1, 199.1
See application file for complete search history.

(56) References Cited

U.S. PATENT DOCUMENTS

| | | | | |
|---|---|---|---|---|
| 7,041,441 | B1 * | 5/2006 | Steven et al. | 435/5 |
| 8,148,130 | B2 * | 4/2012 | Alving et al. | 435/235.1 |
| 2006/0029615 | A1 * | 2/2006 | Ren et al. | 424/200.1 |
| 2008/0274533 | A1 * | 11/2008 | Alving et al. | 435/235.1 |
| 2008/0299082 | A1 * | 12/2008 | Ren et al. | 424/93.2 |
| 2011/0250263 | A1 * | 10/2011 | Rao | 424/450 |
| 2013/0196416 | A1 * | 8/2013 | Rao | 435/235.1 |

OTHER PUBLICATIONS

Cowley. The biology of HIV infection. Leprosy Review Jun. 2001, vol. 72, No. 2, p. 212-220. Abstract only provided.*
Kusumi et al. Human immunodeficiency virus type 1 envelope gene structure and diversity in vivo and after cocultivation in vitro. Journal of Virology, Feb. 1992, vol. 66, No. 2, p. 875-885.*
Friedrich et al. Reversion of CTL escape—variant immunodeficiency viruses in vivo. Nature Medicine Mar. 2004 vol. 10, No. 3, p. 275-281.*
Meyerhans et al. Temporal fluctuations in HIV quasispecies in vivo are not reflected by sequential HIV isolations. Cell 1989, vol. 58, p. 901-910.*
Altman et al. HIV escape: there and back again. Nature Medicine Mar. 2004 vol. 10, No. 3, p. 229-230.*
Derosiers. Prospects for an AIDS vaccine. Nature Medicine Mar. 2004, vol. 10, No. 3, p. 221-223.*
Leslie et al. HIV evolution: CTL escape mutation and reversion after transmission. Nature Medicine Mar. 2004 vol. 10, No. 3, pp. 282-289.*
Aebi U, van Driel R, Bijlenga RK, ten Heggeler B, van den Broek R, Steven AC, Smith PR. Capsid fine structure of T-even bacteriophages. Binding and localization of two dispensable capsid proteins into the P23 surface lattice. J Mol Biol. Mar. 15, 1977;110(4):687-98.*
Pereboeva LA, Pereboev AV, Wang LF, Morris GE. Hepatitis C epitopes from phage-displayed cDNA libraries and improved diagnosis with a chimeric antigen. J Med Virol. Feb. 2000;60(2):144-51.*
Greenwood J, Willis AE, Perham RN. Multiple display of foreign peptides on a filamentous bacteriophage. Peptides from *Plasmodium falciparum* circumsporozoite protein as antigens. J Mol Biol. Aug 20, 1991;220(4):821-7.*
Black, L., et al., "Morphogenesis of the T4 Head," *Molecular Biology of Bacteriophage T4*, American Society for Microbiology, Washington, D.C., pp. 218-258 (1994).
Danner, S.; et al., "T7 Phage Display: A Novel Genetic Selection System for Cloning RNA-binding Proteins from cDNA Libraries," *Proc. Natl. Acad. Sci. USA*, vol. 98, No. 23, pp. 12954-12959 (2001).
Eiserling, F., "Structure of the T4 Virion," *In Bacteriophage T4*, American Society for Microbiology, Washington, D.C., pp. 11-24 (1983).

(Continued)

*Primary Examiner* — Benjamin P Blumel
*Assistant Examiner* — Rachel Gill
(74) *Attorney, Agent, or Firm* — Alchemy-Partners, PC

(57) ABSTRACT

Compositions and methods comprising bacteriophages are provided. In particular, the present invention includes novel and customized T4 bacteriophages uniquely designed for effective antigen and foreign particle presentation. The present invention also provides in vitro methods for the making of customized T4 bacteriophages. The compositions and methods of the present invention may be used for effective vaccine delivery systems.

35 Claims, 12 Drawing Sheets

(56) References Cited

OTHER PUBLICATIONS

Fokine, A., et al., "Molecular Architecture of the Prolate Head of Bacteriophage T4," *Proc. Natl. Acad. Sci. USA*, vol. 101, No. 16, pp. 6003-6008 (2004).

Hoess, R., "Bacteriophage Lambda as a Vehicle for Peptide and Protein Display," *Curr. Pharmac. Biotech.*, vol. 3, No. 1, pp. 23-28 (2002) (Abstract Only).

Ishii, T., et al., "Molecular Organization of the Shell of the $T_{even}$ Bacteriophage Head," *J. Mol. Biol.*, vol. 97 pp. 655-660 (1975).

Ishii, T., et al., "The Two Dispensable Structural Proteins (Soc and Hoc) of the T4 Phage Capside; Their Purification and Properties . . . in vitro," *J. Mol. Biol.*, vol. 109, pp. 487-514 (1977).

Ishii, T., et al., "Binding of the Structural Protein Soc to the Head Shell of Bacteriophage T4," *J. Mol. Biol.*, vol. 120, p. 533-544 (1978).

Iwasaki, K., et al., "Molecular Architecture of Bacteriophage T4 Capsid . . . Accessory Protein, Soc," *Virology*, vol. 271, No. 2, pp. 321-333 (2000) (Abstract Only).

Jiang, J., et al., "Display of a PorA Peptide From *Neisseria meningitidis* on the Bacteriophage T4 Capsid Surface," *Infect. and Immun.*, vol. 65, No. 11, pp. 4770-4777 (1997).

Kuebler, D., et al., "Functional Analysis of the DNA-Packaging/Terminase Protein gp17 from Bacteriophage T4," *J. Mol. Biol.*, vol. 281, No. 5, pp. 803-814 (1998) (Abstract Only).

Leiman, P., et al., "Structure and Morphogenesis of Bacteriophage T4," *Cell. Mol. Life Sci.*, vol. 60, pp. 2356-2370 (2003).

Manoutcharian, K., et al., "Phage Displayed Biomolecules as Preventive and Therapeutic Agents," *Curr. Pharm. Biotech.*, vol. 2, No. 3, pp. 217-223 (2001) (Abstract Only).

Maruyama, I., et al., "λfoo: a λ Phage Vector for the Expression of Foreign Proteins," *Proc. Natl. Acad. Sci. USA*, vol. 91, pp. 8273-8277 (1994).

Rao, V., et al., "DNA Packaging of Bacteriophage T4 Proheads in vitro: Evidence that Prohead Expansion is Not Coupled to DNA Packaging," *J. Mol. Biol.*, vol. 185, No. 3, pp. 565-578 (1985) (Abstract Only).

Rao, V., et al., "The N-Terminal ATPase Site in the Large Terminase Protein gp17 is Critically Required for DNA Packaging in Bacteriophage T4," *J. Mol. Biol.*, vol. 314, No. 3, pp. 401-411 (2001) (Abstract Only).

Rao, V., et al., "A Phage T4 in vitro Packaging System for Cloning Long DNA Molecules," *Gene*, vol. 113, No. 1, pp. 25-33 (1992) (Abstract Only).

Ren, Z., et al., "Phage T4 Soc and Hoc Display of Biologically Active Full-Length Proteins on the Viral Capsid," *Gene*, vol. 215, No. 2, pp. 439-444 (1998) (Abstract Only).

Ren, Z., et al., "Phage of Display of Intact Domains at High Copy Number: A System Based on SOC, the Small Outer Capsid Protein of Bacteriophage T4," *Protein Sci.*, vol. 5, p. 1833-1843 (1996).

Scott, J., et al., "Searching for Peptide Ligands with an Epitope Library," *Science*, vol. 249, No. 4967, pp. 386-390 (1990) (Abstract Only).

Smith, G., et al., "Filamentous Fusion Phage: Novel Expression Vectors That Display Cloned Antigens on the Virion Surface," *Science*, vol. 228, No. 4705, pp. 1315-1317 (1985) (Abstract Only).

Smith, G., et al., "Phage Display," *Chem. Rev.*, vol. 97, No. 2, pp. 391-410 (1997).

Sternberg, N., et al., "Display of Peptides and Proteins on the Surface of Bacteriophage λ," *Proc. Natl. Acad. Sci. USA*, vol. 92, pp. 1609-1613 (1995).

Steven, A., et al., "Structure of T4 Polyheads: A Pathway of Polyhead Transformations as a Model for T4 Capsid Maturation," *J. Mol. Biol.*, vol. 106, pp. 187-221 (1976).

Yanagida, M., "Molecular Organization of the Shell of T-even Bacteriophage Head: Arrangement of Subunits in the Head Shells of Giant Phages," *J. Mol. Biol.*, vol. 109, pp. 515-537 (1977).

International Search Report and Written Opinion, Jan. 20, 2006, Venigalla Basaveswara Rao.

Cullen, P., "Rupture of the Atherosclerotic Plaque: Does a good Animal Model Exist?", Arteriosclerosis Thombosis Vascular Biology, 2003, vol. 23, pp. 535-542.

Humphries, C., "Immunology: Mouse Model Devised that Develops Asthma", Focus, Jan. 2002.

Wei, X., "Antibody Neutralization and Escape by HIV-1", Nature, Mar. 2003, vol. 422, pp. 307-312.

Extended European Search Report received in European Application No. 10158790.5 dated May 12, 2010.

Extended European Search Report received in European Application No. 10158774.9 dated May 12, 2010.

Jennifer Jiang et al., "Display of a PorA Peptide from *Neisseria meningitidis* on the Bacteriophage T4 Capsid Surface", *Infection and Immunity*, vol. 65, No. 11, pp. 4770-4777 (Nov. 1997).

Z.J. Ren et al., "Phage Display of Intact Domains at High Copy Number: A System Based on SOC, the Small Outer Capsid Protein of Bacteriophage T4", *Protein Science*, 5, pp. 1833-1843 (1996).

Zhao-jun Ren et al., "Phage T4 SOC and HOC Display of Biologically Active, Full-Length Proteins on the Viral Capsid", *Gene*, 215, pp. 439-444 (1998).

\* cited by examiner

Example of In Vitro System

Engineer the recombinant antigen into the Hoc/Soc expression vector, express the recombinant antigen in *E. coli*, purify the fusion protein by chromatography on Ni-agarose and other columns Isolated *hoc* and/or *soc*⁻ T4 phage particles

*In vitro* assembly reation

Hexa-histidine tag

Foreign antigen

Hoc/Soc

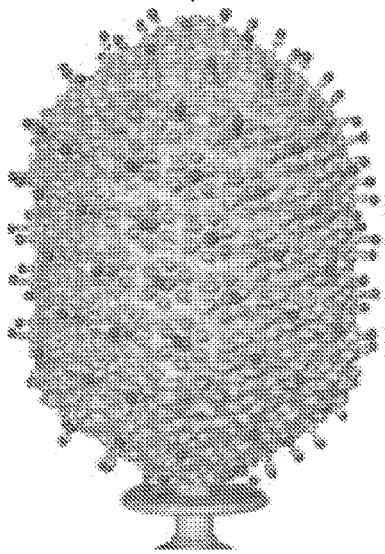

Phage T4 nanoparticles displaying recombinant antigen

FIG. 2

METHODS AND COMPOSITIONS COMPRISING BACTERIOPHAGE NANOPARTICLES

CROSS-REFERENCE TO RELATED APPLICATIONS

The present application claims priority to U.S. Provisional Application Ser. No. 60/530,527 filed Dec. 17, 2003.

FIELD OF THE INVENTION

The present invention is related to a novel methods and compositions comprising bacteriophages. In particular, the present invention includes novel and customized bacteriophages uniquely designed for effective antigen and foreign particle presentation. The methods and compositions of the present invention may be used for effective vaccine delivery systems.

BACKGROUND OF THE INVENTION

In phage display, a foreign peptide, domain, or protein, is fused to a structural protein and exposed on the outer surface of phage capsid (Smith, 1985). The coat proteins of the filamentous phages (M13, fd, and fl), the minor coat protein pIII (4-5 copies), and the major coat protein pVIII (2700 copies), have been extensively used to generate combinatorial libraries of six to eight amino acid long peptides (Smith and Petrenko, 1997; Manoutcharian et al., 2001). Other display systems using icosahedral phages lambda and T7 have also been developed (Maruyama et al., 1994; Danner and Belasco, 2001). These systems can display larger peptides and domains, and even full-length proteins derived from targeted clones or c-DNA libraries (Hoess, 2002). The outer capsid protein gpD (420 copies) (Stemberg and Hoess, 1995) and the tail protein gpV of phage lambda (Maruyama et al., 1994), and the major capsid protein gp10 of phage T3/T7, have been used to display foreign sequences. Rare peptides having a particular biological function can be "fished out" of these libraries by "biopanning" and then amplified (Scott and Smith, 1990; Smith and Petrenko, 1997). The connectivity between phenotype and genotype, i.e., the physical link between the peptide that is displayed on the outside of phage and the DNA that encodes it inside the same phage, allows rapid delineation of the biologically interesting peptide sequence.

Despite the availability of these display systems, significant limitations exist in the application of these systems. For example, with the filamentous phage, display of certain peptides is restricted, or not possible, since the fused peptide has to be secreted through the E. coli membranes as part of the phage assembly apparatus. Since both pIII and pVIII are essential for phage assembly, it is difficult to display large domains or full-length proteins without interfering with their essential biological functions. In situations where large peptide sequences are displayed, their copy number per phage capsid is greatly reduced and unpredictable. Similar problems on the size and copy number are encountered with the phage lambda and T3 display systems. It is often necessary to incorporate wild type protein molecules along with the recombinants to generate viable phage using either a helper phage or a partial genetic suppression of amber mutant (Hoess, 2002; Manoutcharian et al., 2001; Maruyama et al., 1994).

Another serious limitation of existing phage display systems is that they are in vivo-based in that the recombinant molecules are assembled onto the capsid as part of the phage infective cycle. In these systems, many variables in the cellular environment affect the assembly process resulting in great variability in the quality of phage particles generated. Very little control can be exerted on the assembly process and the copy number among different preparations can vary by orders of magnitude making these systems highly unpredictable.

Size and copy number of the displayed antigen are particularly critical variables for vaccine development; thus, the efforts to use phage display for creating a practical vaccine have been quite limited. An ideal phage vaccine would be capable of displaying full-length antigens or desired epitopes of an antigen at a high density without significant restrictions on size. It would also allow manipulation of the display platform in a defined way to generate particles of reproducible quality. What is needed is a first phage system that allows efficient and controlled display of full-length antigens, or epitopes of target antigens using phage T4 particles. Also desirable are phage systems that may be customized to obtain specific immune responses, for example phage systems that enable the generation of an immune response to more than one antigen or foreign particle.

The bacteriophage T4 has been explored for the development of multicomponent vaccines. The capsid of phage T4 is a prolate (elongated) icosahedron (Eiserling, 1983; Black et al., 1994) with a diameter of about 86 nm and a length of about 119.5 nm (Fokine et al., 2004; FIG. 1). It is constituted by 930 copies of a single major capsid protein, gp23* (46 kDa; blue knobs in FIG. 1). The capsid also consists of two minor capsid proteins located at the vertices. Eleven of the 12 vertices are constituted by about 55 copies (one pentamer at each vertex) of the minor capsid protein gp24* (42 kDa; magenta knobs in FIG. 1). The twelfth vertex is constituted by about twelve identical copies (dodecahedron) of the minor capsid protein gp20 (61 kDa; not shown in FIG. 1). This vertex is also referred to as the portal vertex since it serves both as an entry point and as an exit point for T4 DNA.

Structural studies have established that two additional proteins, namely Hoc (Highly antigenic outer capsid protein, 40 kDa) and Soc (Small outer capsid protein, 9 kDa), (FIG. 1) are added onto the capsid after completion of capsid assembly (Steven et al., 1976; Yanagida, 1977; Ishii and Yanagida, 1975 and 1977; Ishii et al., 1978, Iwasaki et al., 2000). According to the most recent structural data reported by Fokine et al. (2004), Hoc is present up to 155 copies per capsid particle, whereas Soc is present up to 810 copies per capsid particle. Most importantly, these proteins are nonessential. Mutations in either of the genes, or in both the genes, do not affect phage production, phage viability, phage infectivity, or phage stability under normal experimental conditions. However, Hoc and Soc provide additional stability to the capsid under extreme environmental conditions (eg., pH>10.6, osmotic shock).

When others first reported Hoc and Soc, it was thought that these proteins represented a new and interesting class of outer capsid proteins that form an outer "cage/armor" to protect the virus in its extracellular phase of the life cycle. Yet, since their discovery, no other phage/virus system has been shown to possess such non-essential, high copy number, highly antigenic, relatively easily manipulable, outer capsid genes.

One useful feature of Hoc and Soc proteins is that one can fuse foreign proteins or protein fragments to the N- and C-termini of Hoc and Soc without affecting T4 phage function. In fact, display of Hoc and Soc fusion proteins does not affect phage viability or infectivity (Jiang et al., 1997; Ren et al., 1996; Ren and Black, 1998). Large polypeptide chains and full-length proteins have been fused to Hoc and Soc and successfully displayed on the T4 capsid surface. These include the Por-A loop-4 peptide (4 kDa), HIV-gp120 V3 loop (5 kDa), soluble CD4-receptor (20 kDa), anti-egg white lysozyme domain (32 kDa), and poliovirus VP1 (35 kDa), (Jiang et al., 1997; Ren et al., 1996; Ren and Black, 1998). Furthermore, the foreign proteins were stably displayed on the capsid, and can be stored for several weeks at 4° C., or in the presence of high salt concentration (Jiang et al., 1997; Ren et al., 1996). The T4 recombinant nanoparticles elicited high titer antibodies in mice against the displayed antigens.

Previous strategies have utilized an unpredictable in vivo loading of foreign proteins onto the phage capsid. This has been the prevailing paradigm in the phage display field using phages M13, lambda, T7 and T4. In one in vivo strategy, the proteins are first expressed in $E.$ $coli$ and then loaded onto T4 following infection with hoc$^-$soc$^-$ virus (Jiang et al., 1997). In a second in vivo strategy, the fusion construct is transferred into the T4 phage genome by recombinational exchange and the fusion protein is expressed and loaded onto phage T4 during the course of T4 infection; in this strategy, the recombinant gene and gene product become a part of phage T4 life cycle (Jiang et al., 1997; Ren et al., 1996). A major drawback of the in vivo loading systems is the variability in the copy number of the displayed antigen. This is largely due to variation of antigen assembly in vivo upon which little control can be exerted. For example, the expression level of recombinant antigen in the infected cell varies greatly depending upon nutritional and environmental conditions. Also, the assembly process is susceptible to nonspecific intracellular proteolysis. Additionally, interactions among numerous components of the intracellular milieu make it a poorly defined process for producing homogeneous particles with consistent quality.

Various Hoc and Soc-based assembly platforms have been conceptualized. For example, in U.S. Pat. No. 6,500,611 issued to Mattson, the inventor describes a general concept for linking a reporter group to a viral capsid wherein the reporter group recognizes an analyte via a linker molecule. Mattson, however, fails to enable specific methods for loading foreign proteins onto a T4 phage capsid. Also, Mattson fails to demonstrate or suggest that large full-length capsid proteins can be loaded at a high density on the capsid surface. Moreover, Mattson fails to teach or suggest T4 nanoparticle vaccine compositions or that any such compositions may be used as a multicomponent platform for eliciting an immunogenic response.

In studies by Ren et al., Protein Science, September; 5(9), 1833-43 (1996), the authors discuss the binding of Soc fusion proteins to capsid-based polymers called polyheads. This polyhead model is particularly unsuited for development of defined assembly platforms and vaccine compositions. Foremost, polyheads are not defined particles. Rather, these polymers result from the uncontrolled growth of phage T4 major capsid protein gp23 and exist as a heterogeneous mixture of particles after their preparation. For example, to even posses Hoc and Soc binding sites, one must cleave polyheads polymers in vitro in the presence of a crude extract containing the phage T4 prehead protease in order to open up the binding sites for Hoc and Soc. The latter also requires "polyhead expansion", a dramatic conformational change that reorganizes the capsid protein polymer and creates the Hoc and Soc binding sites. The resulting cleaved, expanded, polyheads will have ill-defined number of Hoc and Soc binding sites on a structurally heterogeneous mixture of polyheads, whose length can vary anywhere from a few nanometers to micrometers. Unlike T4 phage particles, these polyheads comprise flat, two-dimensional structures; they contain sheets, closed sheets (tubes), and broken pieces of gp23 polymers, etc. of varying size and dimensions. Given this variability of the polyhead model, the number of available binding sites on the particles cannot be determined accurately with undue experimentation. Thus, controlling the copy number of a foreign antigen on the polyheads would be extremely difficult if not impossible. Also, because of their shape, polyheads are not competent to package DNA and can thus not be used a prime-boost strategies known in the art.

What is needed are effective compositions and methods for customizing bacteriophages. Customized bacteriophages may be used to create vaccine systems comprising customized phage particles. Such systems should enable the design of specific phage particles capable of eliciting an immune response to one or more antigens or foreign particles. Preferably, such a system should be easy to manufacture and administer.

What is also needed are compositions and methods to target the exposure or delivery of specific antigens or particles to target cells.

There is also a general need for compositions and improved methods for producing antibodies. These compositions and methods should be easily and economically produced in a manner suitable for therapeutic and diagnostic formulation.

SUMMARY OF THE INVENTION

The present invention comprises effective compositions and methods for producing customized phage particles. Such systems enable the design of specific phage particles capable of eliciting an immune response to one or more antigens or foreign particles and may be used to create novel vaccine delivery systems. In addition, such systems are easy to manufacture and administer.

The unique compositions and methods of the present invention enable customization of phage particles whereby the number and selection of antigen (or antigens) displayed on the phage can be specifically controlled. As such, phage constructed according to the methods described herein may be customized according to the condition to be treated and may contain specific numbers of antigens, and/or specific epitopes of a particular antigen (or antigens). In certain embodiments, labels may be incorporated onto the phage. In certain other embodiments, phage may be customized to generate an immune response for more than one disease where such diseases may manifest close in time (for example, the phage may be customized to treat human immunodeficiency viral infection as well as a mycobacterial infection since AIDs and tuberculosis often occur around the same time).

The vaccine systems of the present invention also enable the exposure or delivery of specific antigens or particles to target cells.

The present invention also comprises improved methods for producing antibodies.

The present invention comprises customized phage particles and methods for making the same wherein such methods are easily and economically produced in a manner suitable for therapeutic and diagnostic use.

The present invention overcomes previous in vivo limitations associated with the manufacture of phage particles by allowing the construction of defined T4 bacteriophage nanoparticles in vitro on a predictable and large-scale basis.

In contrast to a previous polyhead model, the present in vitro loading system utilizes a specifically defined T4 phage particle. In particular, the present invention allows loading of Hoc and/or Soc fusion proteins onto T4 phage particles in a specific and defined way to create a variety of T4 phage nanoparticles for use in a multitude of different applications.

The present invention provides novel in vitro systems enabling the systematic experimentation and customization of the T4 capsid surface. The in vitro systems described herein enable the preparation of defined particles with reproducible biological activity. Importantly, the method of phage construction as described herein accomplishes the specific goal of constructing multi-component vaccines in a streamlined format: enabling the transition from gene to displayed nanoparticle within a short period of time (for example, one to two weeks).

In certain embodiments, the phage or nanoparticles the nanoparticles can be prepared without any DNA (empty capsids), or with the same foreign DNA cloned in the T4 genome (prime-boost strategy).

The in vitro assembly system of the present invention allows the heretofore unavailable production of customized T4 phage nanoparticles on a reliable and large-scale basis.

The in vitro assembly system of the present invention also allows the production of T4 nanoparticles that are capable of presenting large molecules on the T4 phage surface. These molecules can elicit a strong humoral and/or cell-mediated response.

By combining T4 nanoparticles of the present invention that display surface antigens and that possess DNA constructs within the phage genome that encode antigenic proteins, the in vitro assembly system of the present invention provides a method of prime-boost immunization.

Accordingly, it is an object of the present invention to provide methods and compositions for novel and customized bacteriophages.

It is another object of the present invention to provide vaccine delivery systems comprising customized bacteriophages.

Yet another object of the present invention to provide vaccine delivery systems comprising bacteriophages wherein such bacteriophages are customized with specific antigens, antigenic epitopes, markers, labels, proteins, foreign particles, and the like.

Another object of the present invention to provide vaccine delivery systems comprising nanoparticles having specifically defined dimensions and capacity for being loaded with entities such as fusion proteins and the like.

It is a further object of the invention to provide vaccine delivery systems comprising nanoparticles customized to elicit one or more specific immune responses.

An additional object of the present invention is to provide customized delivery vehicles capable of presenting, exposing or delivering particular antigens or other molecules to desired targets.

Yet another object of the present invention is to provide novel vaccine delivery systems that may be administered intramuscularly, intravenously, transdermally, orally, or subcutaneously.

Another object of the present invention is to provide a single T4 nanoparticle that provides immune-based protection against a single or multiplicity of diseases.

Yet another object of the present invention is to provide a single vaccine composition that provides immune-based protection against a multiplicity of different diseases.

An additional object of the present invention is to provide a T4 nanoparticle composition that is capable of displaying large antigenic molecules and eliciting an immune response to these molecules.

Yet another aspect of the present invention is to provide a method of prime-boost immunization wherein T4 phage particles deliver both antigens displayed on the phage particle surface, as well as DNA constructs encoding various antigenic molecules.

Another object of the present invention is to provide a T4 phage assembly platform upon which a plurality of molecules may interact to expose different antigenic domains or to produce other antigenic molecules.

These and other objects, features and advantages of the present invention will become apparent after a review of the following detailed description of the disclosed embodiment and the appended claims.

BRIEF DESCRIPTION OF THE DRAWINGS

FIG. 2 schematically depicts the in vitro assembly system of the present invention and the resultant T4 phage nanoparticles displaying recombinant antigen.

DETAILED DESCRIPTION

Figure 1B:
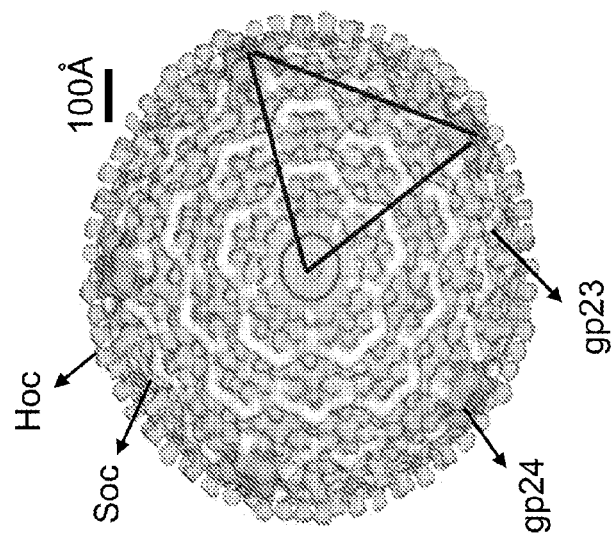
FIG. 1 schematically depicts a color-coded surface representation of the cryo-EM reconstruction of phage T4 capsid: (a) view perpendicular to the 5-fold axis. gp23* is shown in blue, gp24* in magenta, Soc in white, Hoc in yellow and the tail in green; (b) view along the 5-fold axis with the portal vertex towards the observer; the tail part of the reconstruction is shown as green. This figure is reproduced from Fokine et al., 2004. [Prior Art]
Figure 1A:
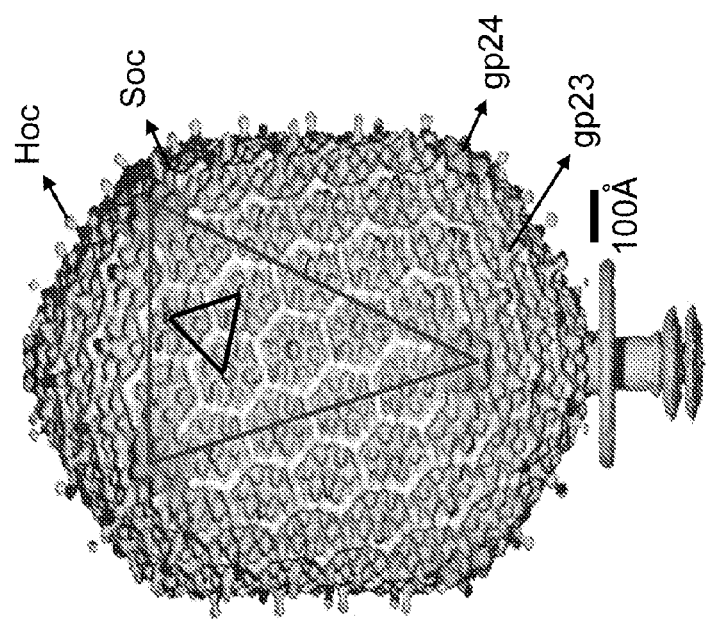

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Application Ser. No. 60/530,527 filed Dec. 17, 2003.

Currently available phage based vaccine systems are limited in they cannot be customized with regard to the volume or identity of antigens displayed. The present invention is the first phage system to enable efficient and controlled display of a variety of antigens (including full-length recombinant antigens) using phage T4 particles. The compositions and methods described herein for producing customized T4 bacteriophage nanoparticles enable the production of uniquely specific vaccines. In addition, the T4 bacteriophage nanoparticles of the present invention are particularly desirable because they facilitate an immune response where the individual protein or other molecules would not.

The present invention comprises customized T4 bacteriophage nanoparticles and methods for making the T4 phage nanoparticle in vitro. In particular, the method for making the T4 phage nanoparticle comprises an in vitro assembly system that utilizes a hoc$^-$ and/or soc$^-$ T4 bacteriophage particle and a Hoc and/or Soc protein or a fragment thereof fused to another molecule. This molecule may comprise any molecule having chemical and/or biological activity, including but not limited to a protein, protein fragment, amino acid, antigen, lipid, antibody, carbohydrate, enzyme, cytokine or chemokine or other inflammatory mediator. One can fuse the molecule to Hoc and/or Soc by any method known to those of skill in the art. When this molecule is fused to a Hoc and/or Soc protein or a fragment thereof, the resulting product comprises a Hoc and/or Soc fusion-molecule. In one embodiment of the present invention, the molecule fused to Hoc and/or Soc is a protein such as a foreign protein, thus creating a Hoc and/or Soc fusion protein. FIG. 2 illustrates an embodiment of the in vitro assembly system and the resultant T4 nanoparticle. In FIG. 2, a Hoc and/or Soc fusion protein is created comprising a foreign antigen (shown in red) and the Hoc and/or Soc protein (shown in blue). After purification, these Hoc and/or Soc fusion proteins are combined with purified hoc$^-$ and/or soc$^-$ T4 phage particles. The resultant T4 nanoparticle displays, for example, foreign antigen (red knobs) fused to the Hoc (shown in the T4 nanoparticle as yellow knobs). The T4 nanoparticle illustrated in this figure is derived from a cryo-EM reconstruction of soc$^-$ T4 phage (courtesy of Drs. Andrei Fokine and Michael Rossmann, Purdue University).

To create the Hoc and/or Soc fusion protein embodiment of the present invention, one fuses the N- or C-terminus of a Hoc and/or Soc protein or fragment thereof to a foreign molecule or entity such as a protein. In certain embodiments of the present invention, a hexahistidine tag sequence is added to the N-terminus of the fusion protein to allow for a single-step purification of the protein-Hoc and/or Soc recombinant protein by Ni-agarose column chromatography. One skilled in the art would recognize that instead of a hexahistidine-tag, one may use numerous other tags known in the art for the purification of the recombinant proteins, including but not limited to glutathione transferase (GST), maltose binding protein (MBP), FLAG, hemaglutinin (HA), and green florescent protein (GFP). The invention further comprises a generic linker sequence between the foreign protein and the Hoc or Soc protein. In certain embodiments, the linker is a structureless linker. Though not wishing to be bound by the following theory, it is thought that the linker sequence minimizes interference by the foreign protein domain on Hoc or Soc folding or assembly to the capsid surface and vice versa. In certain embodiments, the structureless linker preferably comprises a polyglycine linker (pro-gly-gly), but a variety of linkers (structured and structureless) varying in length and in sequence that are known in the art are compatible with the present invention.

The Hoc and/or Soc fusion protein embodiment of the present invention may be constructed using a variety of methods. One skilled in the art will appreciate that multiple genetic and protein engineering methods are available for the construction of the Hoc and/or Soc fusion protein. For example, one may use a PCR-directed Splicing by Overlap Extension (SOE) strategy to engineer the gene constructs encoding the desired fusion protein (Kuebler and Rao, 1998; Rao and Mitchell, 2001). This strategy requires four oligonucleotides (Primers 1-4) and three successive PCRs and is a rapid and powerful strategy for engineering recombinant constructions. Using this strategy, fairly complex gene constructions can be engineered and multiple gene fusions completed in a single day. To include the hexahistidine tag sequence according to certain embodiments of the present invention, one may insert the gene construct in-frame to a hexa-histidine tag of the T7 expression vector.

The T4 phage particle of the present invention comprises a defined prolate (elongated) icosahedron with a diameter of about 70-140 nm and a length of about 90-150 nm. In a particular embodiment, the present invention comprises a T4 phage particle of comprising a defined prolate (elongated) icosahedron with a diameter of about 86 nm and a length of about 119.5 nm. To permit Hoc and/or Soc binding to the capsid of the T4 phage particle, the present invention utilizes a hoc$^-$ and/or soc$^-$ T4 phage mutant that is incapable of expressing Hoc and/or Soc protein; thus, this mutant does not contain Hoc and/or Soc proteins on its capsid surface. The method of creating a hoc$^-$ and/or soc$^-$ T4 phage mutant may be carried out by various methods known in the art (appendices in Karam, J. D. (ed.), *Molecular Biology of Bacteriophage T4*. ASM Press, Washington, D.C.). For use in the in vitro system of the present invention, the hoc$^-$ and/or soc$^-$ T4 phage particles need to be isolated and should be substantially pure. One may isolate these T4 phage particles by any means known in the art, but adequate isolation and purification may be achieved for example through sucrose gradient purification as described in Aebi et al., 1976, and Mooney, D. T., et al. (1987) *J Virol.* 61, 2828-2834.

Following the purification the Hoc and/or Soc fusion proteins according to certain embodiments of the present invention and the isolation of hoc$^-$ and/or soc$^-$ T4 phage particles, the purified Hoc and/or Soc fusion protein is assembled or "loaded" onto the purified hoc$^-$ and/or soc$^-$ T4 phage particles by the novel in vitro assembly system to create T4 nanoparticles. Loading involves the placement of Hoc and/or Soc fusion proteins in close proximity to hoc$^-$ and/or soc$^-$ T4 phage particles so that the Hoc and/or Soc proteins bind to the T4 bacteriophage capsid surface. To facilitate loading of the Hoc and/or Soc fusion proteins onto the hoc$^-$ and/or soc$^-$ T4 phage particles, the purified components are incubated in a reaction buffer for about 1-120 min, preferably for about 20-90 min, more preferably for about 40-70 min, and even more preferably for about 30-60 min. During this incubation period, the reaction buffer temperature may vary, but is preferably around 25-45° C., and more preferably around 32-42° C., and even more preferably around 37° C. As for the reaction buffer, a variety of buffers known in the art are compatible with the present invention. For example, a suitable reaction buffer may comprise a Tris buffered saline at a pH between 7-8, or preferably at a pH between 7.2-7.8, and more preferably at a pH between 7.3-7.5, and even more preferably at a pH around 7.4. Other suitable reaction buffers may include those known those skilled in the art, for example, phosphate buffered saline, hepes buffer, and the like, at a variety of salt concentrations, and/or in the presence of many buffer components such as glycerol, sucrose, ionic and non-ionic detergents.

After incubation of the Hoc and/or Soc fusion proteins with the hoc⁻ and/or soc⁻ T4 phage particles in the reaction buffer, the Hoc and/or Soc fusion protein-hoc⁻ and/or soc⁻ T4 phage nanoparticles are removed from the reaction buffer by methods known to those skilled in the art. For example, the reaction mixture (which includes the purified Hoc and/or Soc fusion proteins, the purified hoc⁻ and/or soc⁻ T4 phage particles, the reaction buffer, and the newly formed T4 nanoparticles) may be centrifuged at 5,000-40,000 rpm for 20-100 min, preferably at around 10,000-20,000 rpm for 40-80 min, and more preferably at around 13,000-16,000 rpm for 55-65 min. The particles can also be recovered through column chromatography or gradient centrifugation techniques. Following the centrifugation or recovery step, the supernatant containing unbound Hoc and/or Soc fusion protein is discarded and the pellet, which contains the newly formed T4 nanoparticles, is washed with reaction buffer or other suitable buffers to remove any unbound fusion protein.

Figure 4:
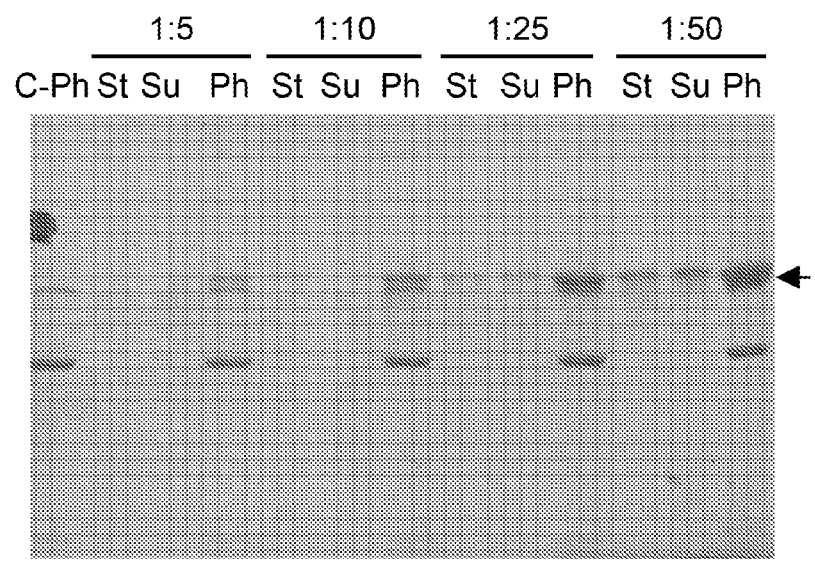
FIG. 4 shows in vitro assembly of HIV-p24-Hoc onto hoc⁻soc⁻ T4 phage particles to create p24 T4 nanoparticles.
Figure 7A:
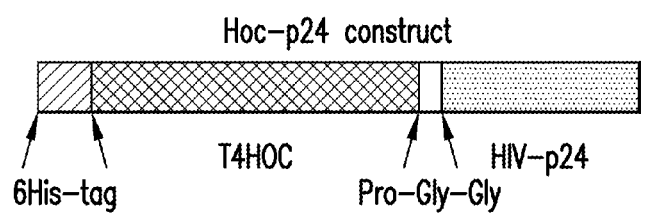
FIG. 7(A) Schematic of Hoc-p24 fusion construct. (B) Expression and purification of Hoc-p24 protein. (C) Results of in vitro assembly experiments for Hoc-p24 protein.
Figure 9:
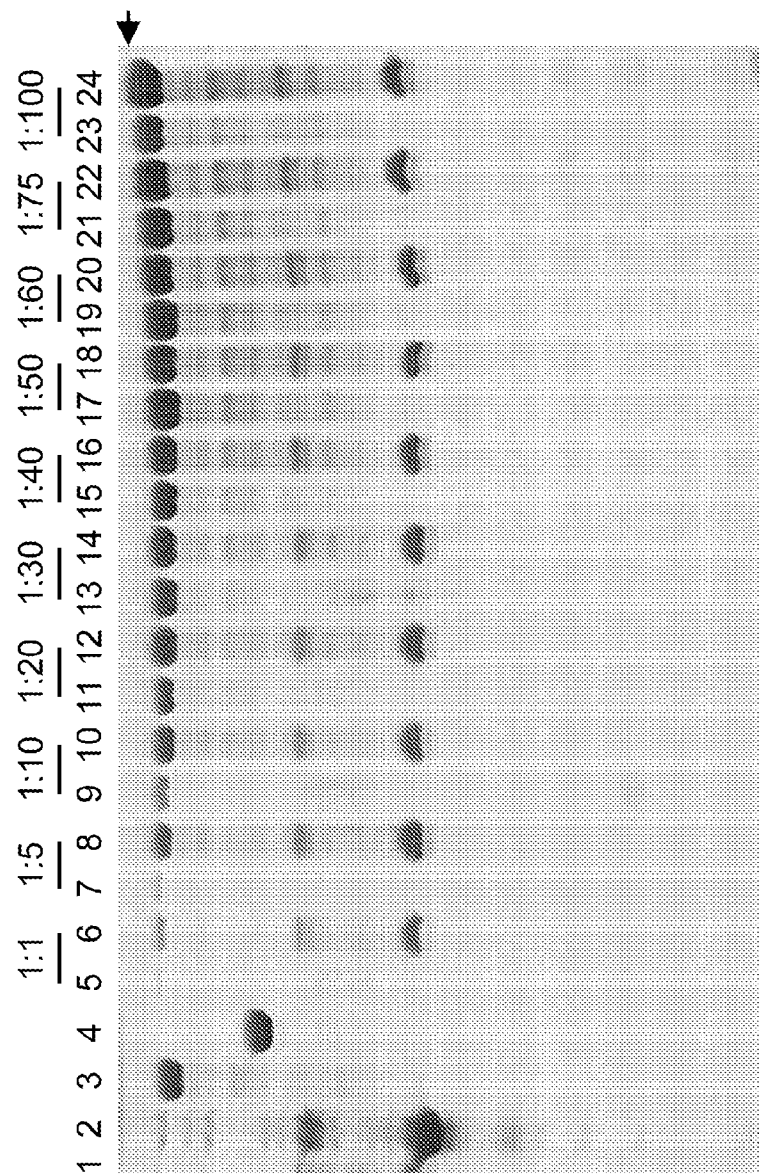
FIG. 9 shows the in vitro assembly of anthrax PA-Hoc on T4 phage nanoparticles.

The T4 phage of the present invention has the advantage of having a defined copy number of Hoc and Soc binding sites (combined total of about 965 copies per particle). With such a large number of defined binding sites, the T4 phage provides a unique nanoplatform upon which one can customize the display of a specific molecule or multiplicity of molecules. As FIGS. 4, 7, and 9 illustrate, by manipulating the ratios of components in the in vitro assembly reaction (i.e., manipulating the ratio of Hoc and/or Soc fusion proteins to T4 phage particles) before or during the incubation period described above, one can control the copy number of fusion proteins bound to the T4 phage particle. This example is illustrated in Example 7. Similarly, by using two or more Hoc and/or Soc fusion proteins in the in vitro assembly system and by adjusting the molar ratios of the different fusion proteins to the T4 phage particles, one can control the proportion of fusion proteins bound to the T4 phage particle to create a defined T4 nanoparticle. For example, a given T4 nanoparticle may display combinations of the HIV antigens tat and nef as well as other fusion proteins. By changing the ratios tat-Hoc and nef-Hoc fusion proteins to phage particles before or during the incubation period, one can correspondingly change the proportion of fusion proteins displayed. Further details of such proteins are provided in Example 8.

Using the in vitro assembly system, one can construct a multitude of different T4 nanoparticle compositions for use in a variety of applications. For example, certain embodiments of the present invention are capable of generating both humoral and cell-mediated immune responses and are thus useful as single or multicomponent vaccine formulations. In these various vaccine formulations, the foreign protein of the Hoc and/or Soc fusion protein may comprise an antigenic protein that is displayed on the surface of a T4 phage particle. Various antigens include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor (TNF-α or b), Transforming Growth Factor-β ("TGF-β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-β"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and heat shock proteins (HSPs); mutant p53; tyrosinase; mucines, such as Muc-1, PSA, TSH, autoimmune antigens; immunotherapy drugs, such as AZT; and angiogenic and anti-angiogenic drugs, such as angiostatin, endostatin, and basic fibroblast growth factor, and vascular endothelial growth factor (VEGF), prostate specific antigen and thyroid stimulating hormone, or fragments thereof. And as described above, by adjusting the molar ratios of Hoc and/or Soc-antigen fusion proteins to hoc⁻ and/or soc⁻ T4 phage particles before or during the incubation period, one may tailor the T4 nanoparticle to display a single antigen, a multiplicity of antigens, and/or a defined proportion of antigens on the capsid of the T4 phage particle. See FIGS. 9 and 10.

In certain embodiments of the present invention, one can use the in vitro assembly system to create T4 nanoparticles that simultaneously display multiple antigens corresponding to one or several infectious diseases. More specifically, by utilizing the in vitro assembly system described herein, one can display, for example, both HIV and anthrax antigens on the same capsid surface, allowing for the formulation of one vaccine against both HIV and anthrax. In another embodiment, the nanoparticle may be customized for diseases and disorders that manifest together or close in time. For example, many AIDS patients suffer from a variety of additional illnesses, such as tuberculosis. A customized nanoparticle could contain an antigen(s) (or various epitopes of an antigen(s)) of human immunodeficiency virus as well as mycobacteria. In an alternative embodiment, one can use the in vitro assembly system to create T4 nanoparticles that simultaneously display multiple epitopes of one, or more than one, antigen on the same capsid.

In another embodiment, site-directed combinatorial mutations can be introduced at the targeted sequence during the construction of Hoc and/or Soc gene fusion constructs (see Rao and Mitchell (2001) for the combinatorial mutagenesis strategy). Using this strategy, expression of a pool of antigen mutants and their combined display on the T4 nanoparticle or on multiple T4 nanoparticles will allow construction of a multi-variant vaccine that would be effective against several strains of an infectious agent, or an infectious agent that generates mutants against the selection pressure of the host (eg., HIV).

In yet another embodiment, one may construct a T4 nanoparticle composition that displays interactive molecules on its surface. For instance, using methods known to those of skill in art, one can construct a first Hoc and/or Soc fusion protein that comprises Hoc and/or Soc fused to a first foreign protein. Similarly, one can construct a second Hoc and/or Soc fusion protein that comprises Hoc and/or Soc fused to a second foreign protein. By employing the in vitro assembly system disclosed herein, one can load both first and second Hoc and/or Soc fusion proteins onto the surface of a T4 phage particle. In certain embodiments, the first and second foreign proteins can individually present various immunological epitopes. Additionally, the first and second foreign proteins may interact with each other directly or indirectly through another protein or molecular component that can be added to the assembly reaction mixture. A T4 nanoparticle composition of this embodiment may, for example, impart, additional immunogenicity to various T4 nanoparticle compositions of the present invention. Not wishing to be bound by the following theory, interactions between the first and second foreign proteins may, for example, expose additional epitopes and therefore enhance the immunogenic response. In a related embodiment, the first foreign protein may possess enzymatic activity while the second foreign protein may serve as a substrate or a ligand for the first foreign protein. In this embodiment, cleavage of the second protein may result in a variety of biological effects, including but not limited to the display of additional epitopes on the T4 nanoparticle surface. Also, the cleaved protein in such an embodiment may, for example, be a cytokine or chemokine that can further modulate the immune response. Although the above embodiments refer to first and second foreign proteins, the present invention also contemplates similar embodiments relying on a multiplicity of different foreign proteins. For example, a third foreign protein and a fourth foreign protein may also display additional epitopes individually and/or when interacting on the surface of the T4 phage particle. Protein engineering techniques known to those of skill in the art will allow manipulation of the structures of, and distances between, the displayed molecular components of these embodiments for a variety of specific applications. These are particularly important because the complexes envisioned either mimic, or are identical to, the native complex(es) formed in vivo through conformational transitions that occur following specific interactions. Such complexes likely generate specific immune responses that can interfere with the interactions between the infectious agent and the host cell (eg., HIV infection of target host cells), the molecules of a multicomponent toxin to generate lethal toxicity (eg., formation of anthrax lethal toxin and edema toxin).

In another embodiment of the present invention, the T4 nanoparticles may comprise a second layer of molecules displayed over a first layer of displayed proteins. In this embodiment, the Hoc and/or Soc fusion proteins may comprise the first layer, and the foreign protein of the Hoc and/or Soc fusion protein serves as a nexus for the assembly of the second layer of molecular components. As such, the displayed first layer proteins can be used as binding sites to display second layer proteins that interact with these first layer binding sites. For instance, T4 nanoparticle-bound anthrax PA63 can be used to capture anthrax lethal toxin and edema toxin (not fused to Hoc or Soc), or a foreign protein that is fused to the N-terminal PA63 binding domain of LF or EF.

In yet another embodiment, one can design T4 nanoparticles that target specific cell or tissue types. In particular, by displaying a Hoc and/or Soc-ligand fusion in which the ligand is specific for a cell and/or tissue type, one can target the T4 nanoparticle of the present invention to certain cells or tissues to elicit a variety of selective cellular or tissue responses. One can develop such a Hoc and/or Soc-ligand fusion molecule by any method known to those of skill in the art. Once developed, the Hoc and/or Soc-ligand fusion molecule can be loaded onto the hoc$^-$ and/or soc$^-$ T4 phage particles using the in vitro assembly system disclosed herein to create T4 nanoparticles displaying the ligand. Various ligands include, but are not limited to the ones that bind to CD4, chemokine receptors, GM-1 receptor, Toll-like/pathogen recognition receptors, DC-sign receptor, cytokine receptor, Fc receptor, or compliment receptors or fragments thereof.

In another embodiment of the present invention, one can use recombinant DNA technology and T4 genetics to package foreign DNA into the T4 nanoparticle's genome (Rao et al., 1992; Clark et al. FEMS *Immunology and Medical Microbiology* 40 (2004) 21-26; March et al. *Vaccine* 22 (2004) 1666-1671). Thus, in addition to the display of Hoc and/or Soc fusion proteins on the surface of the T4 nanoparticle, a foreign DNA construct encoding an antigen or a Hoc and/or Soc fusion protein is present within the T4 nanoparticle. In certain embodiments, such a unique T4 nanoparticle platform technology can be used as a prime-boost delivery system. Generally, the immune responses obtained by plasmid DNA vaccination are poor and inconsistent; thus, multiple injections and large quantities of DNA and protein are required to enhance the immune responses. In contrast, the T4 nanoparticles of this embodiment can deliver both the protein and the DNA components simultaneously to the same antigen-presenting cell, thus potentially inducing more robust immune responses. For example, using phage genetics and molecular biology techniques known in the art, one could insert a DNA construct into the genome of a T4 phage under the control of a strong mammalian promoter such as the CMV (cyto megalo virus) promoter, which would express a fusion protein comprising the HIV antigen nef (i.e., the DNA construct would express a nef-Hoc fusion protein). Alternatively, by using specialized T4 packaging systems (Leffers, G. and Rao, V. B. (1996) A discontinuous headful packaging model for packaging less than headful length DNA molecules by bacteriophage T4. J. Mol. Biol. 258, 839-850), the entire phage T4 genome could be replaced with multiple copies of concatemeric foreign DNA construct. By incubating these genetically modified T4 phages with, for example, fusion proteins comprising Hoc fused to the HIV antigen nef in the in vitro assembly system of the present invention, one could create a novel T4 nanoparticle that comprises DNA encoding a particular antigen inside and the corresponding antigen displayed outside on the capsid surface. As would be appreciated by those skilled in the art, a number of combinations of this embodiment, including multiple genes cloned inside and expressed outside can be envisioned.

In yet another embodiment, one can use the T4 nanoparticles of the present invention to accomplish further modulation of immune responses. For example, one may incorporate various inflammatory mediators onto the T4 nanoparticle platform that amplify the immune response. Such inflammatory mediators include, but are not limited to, various cytokines such as interleukins, lymphokines, tumor necrosis factor, and interferons, as well as other inflammatory mediators such as chemokines. Utilizing the in vitro assembly system of the present invention, one may display these inflammatory mediators, either full-length or the functional motifs and domains, on the T4 nanoparticle surface, or, in other embodiments, one may incorporate DNA constructs encoding inflammatory mediators into the genome of the T4 bacteriophage.

Another embodiment of the present invention comprises T4 nanoparticles that are devoid of packaged DNA. For example, by manipulating T4 genetics (eg., packaging-defective mutations in genes 16 and 17) through methods known to those of skill in the art, one can produce hoc$^-$ and/or soc$^-$ T4 phage mutants that are devoid of packaged DNA (Rao and Black, 1985). Using the in vitro loading system of the present invention, one can then load Hoc and/or Soc fusion proteins onto the hoc$^-$ and/or soc$^-$ T4 phage mutants to create T4 nanoparticles that are devoid of DNA. One can use the T4 nanoparticles of this embodiment as an alternative to DNA-containing T4 nanoparticles when the presence of DNA is a biosafety concern. And because this embodiment does not affect the molecular constituents of the T4 phage capsid surface, one can use this strategy in combination with many of the embodiments disclosed herein.

Another embodiment of the present invention comprises a mixture of various T4 nanoparticles. In this embodiment, one can mix T4 nanoparticles according to any of the embodiments described herein with other, different T4 nanoparticles of the present invention. For example, a vaccine composition against both anthrax and HIV may comprise an HIV-antigen displayed separately on one set of T4 nanoparticles and an anthrax antigen displayed separately on another set of T4 nanoparticle, with each set of nanoparticles created using the in vitro assembly system of the present invention. Using this approach, one could, for example, create a single multicomponent vaccine formulation against a variety of infections different diseases.

In another embodiment, the T4 nanoparticle system of the present invention can also be developed as a unique molecular diagnostic system by exploiting the displayed molecules to detect pathogens/components through specific interactions.

In another embodiment, the displayed antigens can generate additional (synergestic) responses such as antitoxin effects plus immune responses. For instance, the displayed antigens can serve as antitoxins as well as efficacious vaccines at the same time. In the case of an anthrax spore attack, antibiotic treatment as well as vaccine administration are necessary. The immediate use of antibiotic will inhibit (eliminate) the progress of the on-going *B. anthracis* bacterial infection. But, a fraction of the spores can remain in the body for weeks (or months) and cause subsequent infection(s). Thus, vaccination is also necessary in order to neutralize the latter infection. Immunization with phage T4 displaying an antitoxin(s), for instance the PA63-binding N-terminal domain of LF and/or EF, the toxic effects of the initial infection can be neutralized immediately by interfering with the formation of lethal toxin and edema toxin. High density display of the domain (810 copies per capsid in the case of Soc-LF domain fusion) will serve as a polyvalent toxin inhibitor, thus greatly enhancing the affinity to bind to PA63 and neutralize the toxin formation (Nourez, M., Kane, R. S., Mogridge, J., Metallo, S., Deschatelets, P., Sellman, B. R., Whitesides, G. M. and Collier, R. J. (2001) Designing a polyvalent inhibitor of anthrax toxin. *Nature Biotech.* 19, 958-961). The same T4 particles alone, or in combination with an additional T4 nanoparticle (eg., PA-Hoc-T4), administered at the same time, will also serve as a vaccine generating neutralization immune responses and eliminate subsequent infection resulting from delayed spore germination.

Formulations

The vaccine delivery systems of the present invention can be prepared in a physiologically acceptable formulation, such as in a pharmaceutically acceptable carrier, using known techniques. For example, the customized bacteriophage particles may be combined with a pharmaceutically acceptable excipient to form an immunogenic composition.

Alternatively, the bacteriophage particles may be administered in a vehicle having specificity for a target site, such as a tumor or infection.

The vaccine delivery vehicles of the present invention may be administered in the form of a solid, liquid or aerosol. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The bacteriophage compositions may be administered by standard routes of administration. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The dosage of the vaccine composition will depend on the condition being treated, the particular composition used, and other clinical factors such as weight and condition of the patient, and the route of administration.

Diseases and Conditions to be Treated

The methods and compositions described herein are useful for treating human and animal diseases and processes including but not limited to bacterial disease, fungal disease, rickettsial disease, chlamydial disease, viral disease parasitic infection, sexually transmitted diseases, sarcoidosis, and prion disease. The methods and compositions described herein are also useful for treating any disease or disorder mandating an immune response.

The following examples illustrate various embodiments and aspects of the present invention, but are not to be construed as limiting the scope of the present invention in any way. And although the following examples employ Hoc fusion constructs, the present invention can be readily extended to display Soc fusions. In particular, a T4 nanoparticle can accommodate about 810 copies of Soc molecules on the capsid surface, all of which can be replaced by antigens fused to Soc using the in vitro assembly system. In addition, the T4 nanoparticle theme can be extended to include modifications to the major capsid protein itself (930 copies), major tail protein gp18 (144 copies), making it a highly versatile system for vaccine development.

EXAMPLE 1

Construction, Over-Expression, and Purification of p24-Hoc

The DNA fragment corresponding to the full-length p24 polypeptide (225 amino acids, 24 kDa) was joined to the 5'-end of the hoc gene via a DNA sequence encoding a pro-gly-gly linker sequence. As mentioned above, p24 is the major capsid subunit of HIV shell that encapsulated two molecules of HIV genome and other protein (eg., reverse transcriptase, integrase) and nucleic acid (eg., tryptophan tRNA primer) constituents that are essential for infection.

Figure 3A:
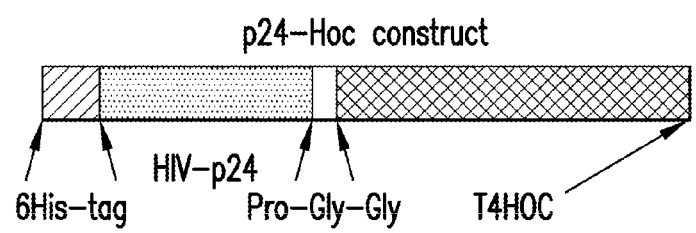
FIG. 3(A) provides a schematic of the HIV-p24-Hoc fusion construct as described in the text. P24 is the major capsid subunit of HIV shell that encapsulated two molecules of HIV genome and other protein (eg., reverse transcriptase, integrase) and nucleic acid (eg., tryptophan tRNA primer) constituents that are essential for infection. (B) shows the expression and purification of p24-Hoc protein.
Figure 3B:
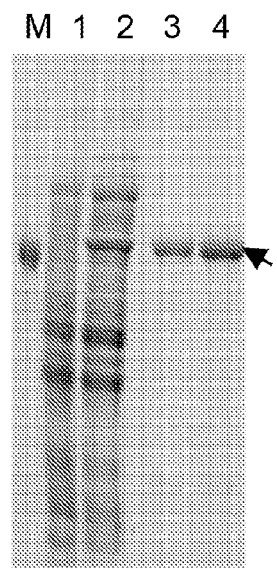

This was carried out by the SOE strategy disclosed in Kuebler and Rao, 1998. In-frame insertion of the construct into the BamHI site of the T7 expression vector pET15b (Novagen Inc. Madison, Wis., USA) resulted in the attachment of a 26 amino acid sequence consisting of hexa-histidine tag to the N-terminus of p24-Hoc protein sequence (FIG. 3(A)). The 66 kDa hexaHis-p24-Hoc fusion protein was expressed to about 10% of the total *E. coli* cell protein by IPTG induction (FIG. 3*b*), and 80% of the expressed protein partitioned into the soluble fraction. The protein was purified to 90% purity by chromatography on Ni-agarose column (FIG. 3(B)). About 8-10 mg purified p24-Hoc was obtained from one liter of culture. In FIG. 3(B), the samples were electrophoresed on a 4-20% SDS-polyacrylamide gel and stained with Coomassie blue; lanes 1 and 2 correspond to *E. coli* samples either before (0 hr) or after (3 hr) IPTG induction of p24-Hoc. Note the appearance of 66 kDa p24-Hoc band upon IPTG induction (arrow). Lanes 3 and 4 show purified protein fractions following Ni-agarose column chromatography.

EXAMPLE 2

In vitro Assembly of T4 Nanoparticles

To assemble or "load" recombinant antigens on the surface of T4 phage particles, about $2\times10^{10}$ sucrose gradient-purified hoc⁻soc⁻ T4 nanoparticles were incubated with increasing amounts of purified HIV-p24-Hoc in TMG buffer (50 mM sodium phosphate buffer, pH 7.0, 75 mM NaCl and 1 mM MgSO$_4$) at 37° C. for about 60 min. The resultant T4 nanoparticles were then sedimented at 14,000 rpm for 60 min and the unbound supernatant fraction was discarded. The particulate pellet was washed twice with excess buffer to remove any unbound or nonspecifically trapped protein. All the samples, the starting material, the unbound and bound fractions, and the controls, were analyzed by 4-20% sodium dodecyl sulfate poly-acrylamide gel electrophoresis (SDS-PAGE) and stained with Coomassie blue. Referring to FIG. 4, the ratio of HIV-p24-Hoc to Hoc binding sites is indicated on the top of the figure. The lanes are as follows: St, starting p24-Hoc; Su, p24-Hoc in the supernatant following binding; Ph, phage nanoparticles. The first C-Ph lane on the left of the figure represents control phage nanoparticles prior to assembly. The rest of the "Ph" lanes correspond to phage nanoparticles following assembly of recombinant antigen at the ratio indicated. This sequence of gel loading is maintained in the other examples. The bands in St and Su lanes are fainter because only about 1/10th of the sample volume could be loaded on the gel due to the limited capacity of each well (20 ul). As shown in FIG. 4, the p24-Hoc efficiently assembled onto the hoc⁻soc⁻ particles to form T4 nanoparticles in the in vitro system. When compared to the control hoc⁻soc⁻ T4 particles (1st c-Ph lane on the left of panel), a new band (arrow) corresponding the p24-Hoc polypeptide appeared upon incubation with p24-Hoc (corresponding to the arrow, Ph lanes under ratios 1:5. 1:10, 1:25, and 1:50). The intensity of this band increases with increasing ratio of p24-Hoc:Hoc binding sites, indicating that one can control the degree of loading by controlling the ratio of p24-Hoc:Hoc binding sites.

EXAMPLE 3

Specificity and Stability of the in vitro Assembly System

Figures 5, 6:
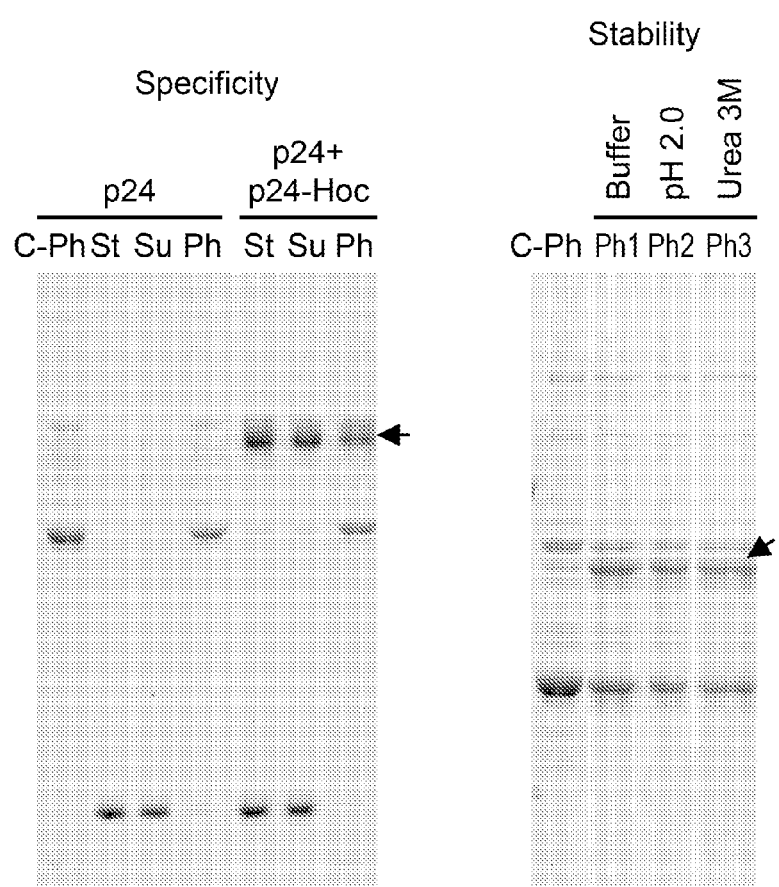
FIG. 5 shows the specificity of p24-Hoc binding to hoc⁻soc⁻ T4 nanoparticles.
FIG. 6 illustrates the stability of the p24-Hoc displayed on hoc⁻soc⁻ T4 nanoparticles.

The binding interaction between p24-Hoc and hoc⁻soc⁻ T4 nanoparticles is highly specific. This specificity is illustrated in FIG. 5. Using the experimental design of Example 2, the T4 nanoparticles were incubated either with p24 alone (lanes 2-4) or a mixture of p24 and p24-Hoc (lanes 5-7). When compared to the control phage (lane 1, C-Ph), p24 bound to the particles only when it is fused with Hoc (lanes 5-7). Note that no significant binding of p24 occurred. The position of p24-Hoc is labeled with an arrow. These results show that fusion to the Hoc polypeptide or fragments thereof is necessary for binding to the T4 particle. Neither of the control proteins, BSA (66 kDa) nor anthrax PA (89 kDa), showed significant binding to the T4 particles (data not shown).

The stability of interactions between the displayed p24-Hoc and T4 phage particles was evaluated by treating the p24-T4 nanoparticles with pH 2.0 buffer or 6M urea, and determining whether any of the bound antigen dissociated. Specifically, p24-Hoc bound T4 nanoparticles were washed with TMG buffer (lane 2) or with pH 2 buffer (lane 3) or 3M urea (lane 4) (FIG. 6). SDS-PAGE of the particles showed that the bound p24-Hoc was stable to both the treatments. Lane C-Ph shows control hoc⁻soc⁻ phage. The position of p24-Hoc is marked with an arrow. Because no significant dissociation occurred in these experiments, these data show that the displayed antigen stringently binds to the T4 phage particle (FIG. 6).

EXAMPLE 4

Use of N- or C Termini of Hoc to Display p24

Both the N- and C-termini of Hoc can be used to display p24. For example, in addition to the N-terminal fusion protein described in Example 1, a reverse C-terminal fusion protein was constructed. To create the C-terminal fusion protein, DNA corresponding to the full length p24 polypeptide was joined in-frame to 3'-end of the hoc gene via a C-terminal-linked DNA sequence encoding a pro-gly-gly linker sequence. The 5'-end of the hoc gene was joined to the sequence encoding hexahistidine tag protein sequence (FIG. 7(A)). The hexaHis-Hoc-p24 was expressed and purified in the same way as the N-terminal fusion (FIG. 7B; Lanes 1 and 2 correspond to *E. coli* samples either before (0 hr) or after (3 hr) IPTG induction of p24-Hoc, respectively. Note the appearance of 66 kDa Hoc-p24 band upon IPTG induction (arrow). Lanes 3 and 4 show purified protein fractions following Ni-agarose column chromatography).

Figures 7B, 7C:
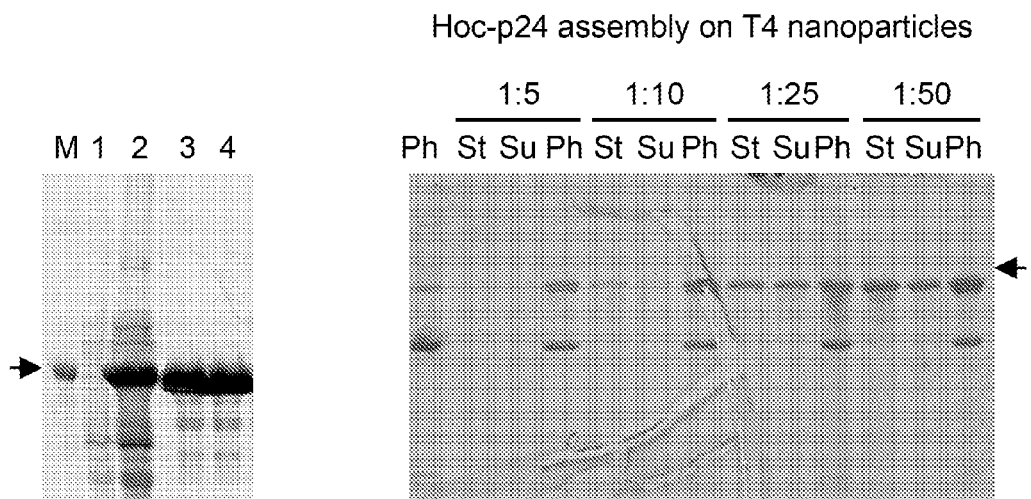

In vitro assembly experiments showed that the Hoc-p24 efficiently assembled onto the capsid surface (FIG. 7(C)), suggesting that neither the N-terminal nor the C-terminal fusion impaired the binding of Hoc to the capsid. Referring to FIG. 7(C), the experimental details are the same as in Example 2, except that purified Hoc-p24 was used in the binding experiment. The ratio of Hoc-p24 to Hoc binding sites is indicated along the top of the Figure. Note the appearance of the new p24-Hoc band in the nanoparticles (arrow). The lanes are as follows: st, starting p24-Hoc; su, p24-Hoc in the supernatant following binding; c-ph, control phage nanoparticles, Ph, phage nanoparticles at different ratios indicated at the top. The samples in Figure (B) and Figure (C) were electrophoresed on a 4-20% SDS-polyacrylamide gel and stained with Coomassie blue.

EXAMPLE 5

Copy Number of the Displayed Antigen

The maximum copy number of p24-Hoc or Hoc-p24, as quantitated by laser densitometry (Molecular Dynamics Inc.), is about 900 p24-Hoc molecules per T4 nanoparticle. This is consistent with gel filtration experiments (data not shown), which showed that the over-expressed Hoc protein exists in solution as a hexamer. Thus, it is likely that there is one hexamer of bound antigen per each gp23 hexamer. The same behavior has also been observed with a number of HIV antigens and the anthrax protective antigen (see Examples below). Given the high-density display of recombinant antigen on the T4 nanoparticle, and the ability to control the copy number by changing the ratios of components in the in vitro assembly reaction (FIGS. 4-7), one can construct a multiplicity of T4 nanoparticles for use in a variety of applications.

EXAMPLE 6

Display of tat and nef on the T4 Nanoparticle

Figure 8A:
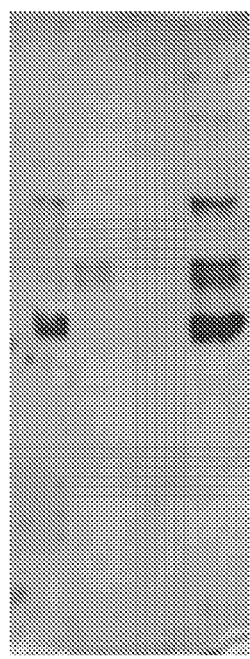
FIG. 8 illustrates the in vitro assembly of (A) HIV tat-Hoc and (B) HIV nef-Hoc (arrows) onto hoc⁻soc⁻ phage T4 nanoparticles.
Figure 8B:
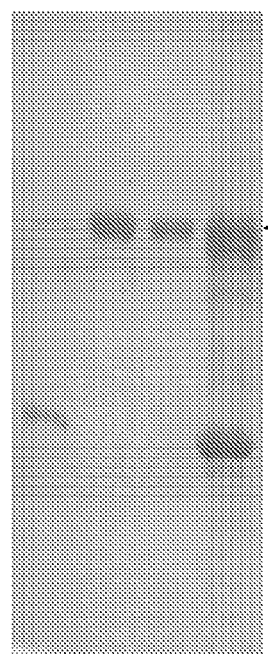

The broad applicability of the in vitro system for antigen display was assessed by constructing fusions with other HIV antigens: tat (10 kDa)-Hoc and nef (30 kDa)-Hoc. Both tat and nef are considered to be important targets for vaccine development against HIV. Assembly of T4 nanoparticles was carried out using the in vitro assembly system as illustrated in Example 2. Referring to FIG. 8, the lanes are as follows: st, starting tat/nef-Hoc; su, tat/nef-Hoc in the supernatant following binding; ph, phage nanoparticles; "c-" represents control. These data clearly demonstrate that both antigens are efficiently displayed on T4 nanoparticles (Figure (A): tat; Figure (B): nef) at the same copy number as p24-Hoc.

EXAMPLE 7

Display of Anthrax Protective Antigen

The 83 kDa protective antigen (PA) from *B. anthracis* is a critical component of the tripartite anthrax toxin. It has been the primary target for developing an efficacious recombinant vaccine against a potential bioterrorist anthrax attack. The T4 nanoparticle platform described herein was applied to display the 125 kDa PA-Hoc fusion protein.

Using the in vitro assembly system of the present invention, PA-Hoc fusion protein was over-expressed up to about 15% of total *E. coli* protein and purified by Ni-agarose chromatography. Referring to FIG. 9, about $10^{10}$ hoc⁻soc⁻ T4 phage particles (lane 1) were incubated with PA-Hoc (arrow) at the ratios indicated along the top of the gel. Following assembly, the samples were electrophoresed on a 4-20% SDS-PAG and stained with Coomassie blue. The supernatant (unbound) (lanes 5, 7, 9, 11, 13, 15, 17, 19, 21, 23) and phage-bound (lanes 6, 8, 10, 12, 14, 16, 18, 20, 22, 24) PA-Hoc show efficient loading of PA-Hoc onto T4 nanoparticles. Lanes 1-3, standards; lane 1, hoc⁻soc⁻ phage; lane 2, purified PA-Hoc; lane 3, purified PA. The fact that a polypeptide as large as 83 kDa PA is displayed at the same high density as p24 suggests that there are no fundamental limitations with respect to size to display proteins on T4 nanoparticles. No other phage display system was shown to be as robust as the in vitro T4 system described here.

EXAMPLE 8

Display of Multiple Antigens

Figures 10A, 10B, 10C:
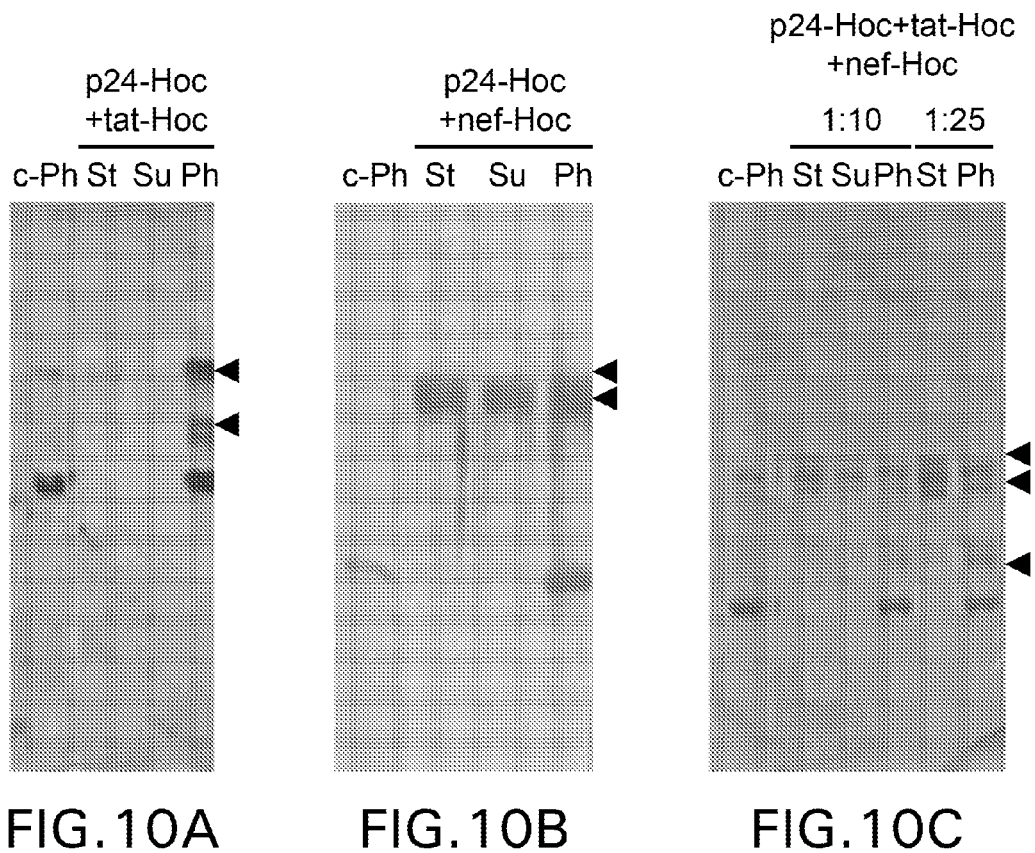
FIG. 10 shows the in vitro assembly of multiple antigens onto hoc-soc-T4 nanoparticles: (A) tat-Hoc and p24-Hoc; (B) nef-Hoc and p24-Hoc; (C) tat-Hoc, nef-Hoc, and p24-Hoc.

The in vitro assembly system of the present invention was carried out in the presence of two antigens, tat-Hoc and p24-Hoc, or nef-Hoc and p24-Hoc, or three antigens, p24-Hoc, tat-Hoc, and nef-Hoc. Referring to FIG. 10, the lanes are as follows: st, starting proteins; su, proteins remaining in the supernatant following binding; ph, phage; c-, control. Arrows show the positions of bound antigens. These data demonstrated that multiple antigens can be loaded onto the capsid surface with the same ease as when it was carried out independently with single antigens (FIGS. 10(A), (B), and (C)). Changing the ratios of the added antigens correspondingly altered the copy number of the antigens on the capsid surface (FIG. 10(C) and data not shown). Quantitative data suggest that all the proteins tested showed comparable binding affinity, indicating that the fused antigen does not significantly influence the binding of Hoc to the nanoparticle.

EXAMPLE 9

Immunogenicity of p24-Hoc T4 Nanoparticles

Figure 11:
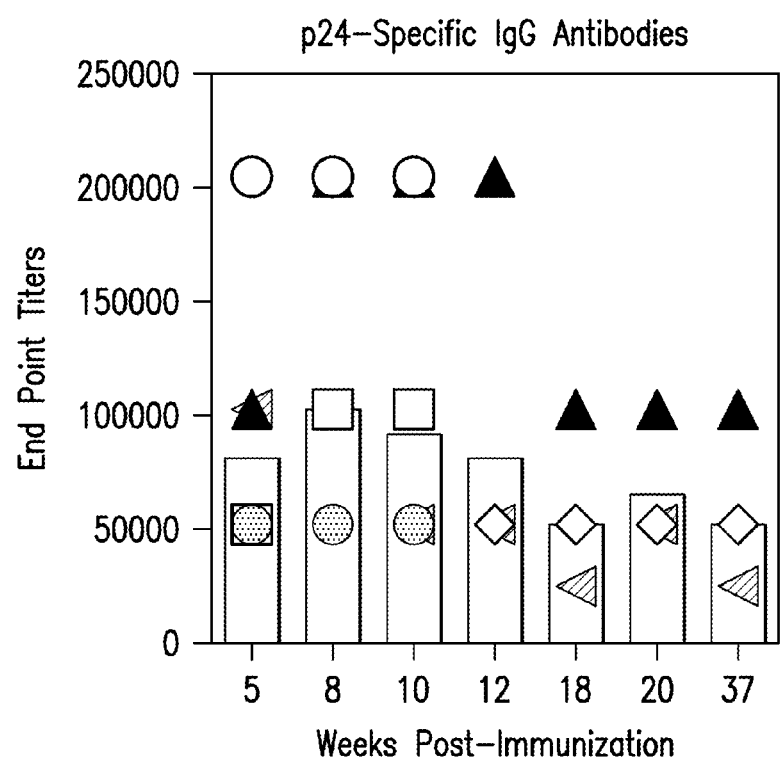
FIG. 11 shows the immunogenicity of p24 displayed on T4 nanoparticles at various time points after immunization.

To test the immunogenicity of T4 nanoparticles, BALB/C mice were immunized on weeks 0, 3, and 6, with <1 µg of p24-Hoc displayed on phage T4. Individual serum samples were analyzed in triplicates for p24-specific IgG antibodies by an enzyme linked immunosorbent assay (ELISA) using baculovirus-expressed p24 as the coating antigen. The data are expressed as end point titers, with the titer being defined as the highest dilution that yielded an OD reading>twice the background values. The titers were calculated after subtracting the mean absorbance of triplicate wells lacking antigen from the absorbance of triplicate wells containing antigen at each serum dilution. FIG. 11 shows the geometric mean end point antibody titers and the symbols represent the individual mouse serum titers.

As FIG. 11 shows, the p24-Hoc-T4 nanoparticles are highly immunogenic in mice. Mice immunized with 10 µg soluble p24 alone induced poor antibody response (titers less than 800 at week 6, data not shown). But, when it is displayed on T4 nanoparticles, a 100-fold increase in p24-specific antibody titers was obtained with <1 µg of displayed antigen, thus demonstrating the strong immunogenicity of p24-T4 nanoparticles. As shown in FIG. 11, end point titers up to 200,000 were obtained with Hoc-p24-T4 nanoparticles. Furthermore, the antibodies induced were long lasting and titers of 50,000 were obtained even after 37 weeks post-immunization. Similar results were obtained with p24-Hoc T4 particles (data not shown) and PA-Hoc T4 particles (see below). It is important to note that the recombinant nanoparticles were directly injected without any added adjuvant. Thus, the T4 nanoparticles, in addition to their role as vaccine delivery vehicles, apparently provided an adjuvant effect thereby generating strong antibody titers against the displayed antigen.

EXAMPLE 10

Immunogenicity of PA-Hoc T4 Nanoparticles

Figure 12:
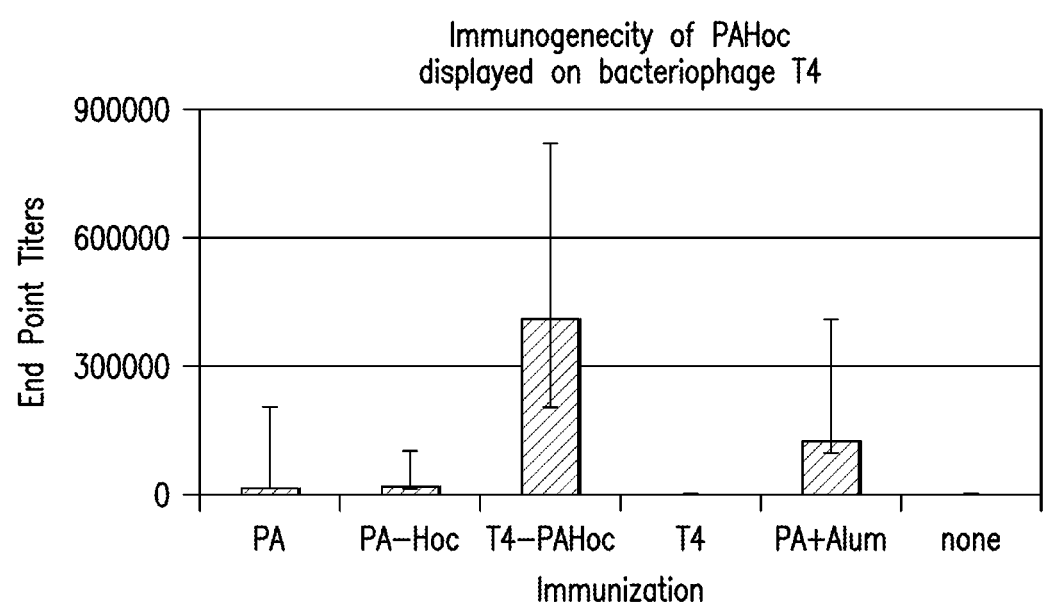
FIG. 12 shows the immunogenicity of T4-displayed PA-Hoc.
Figure 13A:
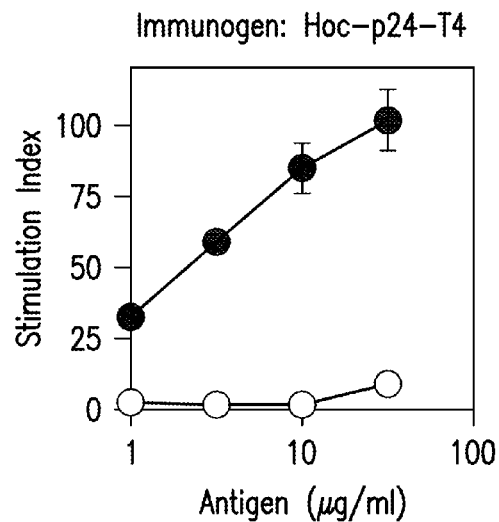
FIG. 13 shows that p24-T4 nanoparticles elicit robust cellular responses.
Figure 13B:
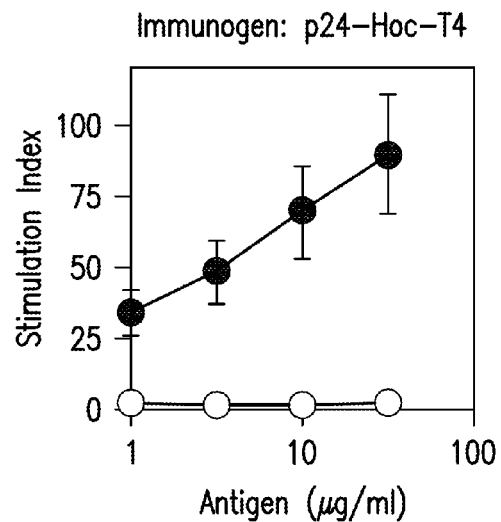
Figure 13C:
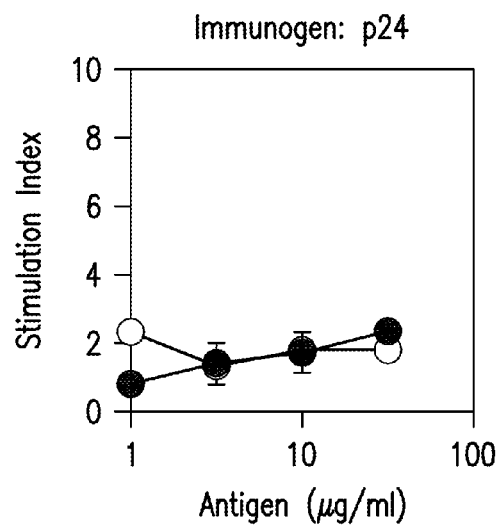
Figure 13D:
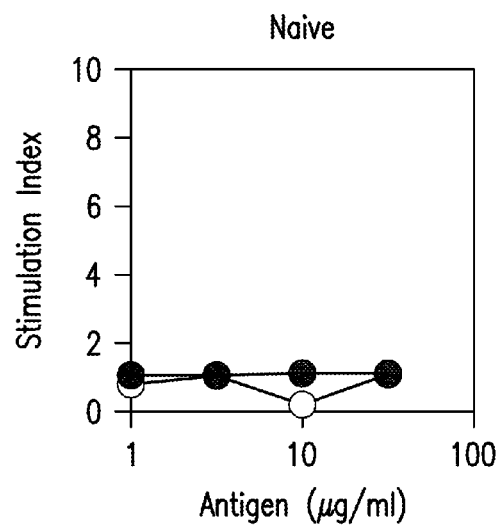

Independent immunogenicity experiments with the displayed anthrax PA-Hoc T4 nanoparticles confirmed that the T4 nanoparticles indeed elicit strong antibody responses. Referring to FIG. 12, this Figure shows PA-specific IgG serum antibodies in CBA/J mice at 8 week-post immunization. The bars represent the geometric mean titers. (Note: error bars indicate range of data, N=10). Mice were injected intramuscularly with PA-Hoc-T4, PA-alum, and a number of controls. (10 mice per each group) In each case, antigen equivalent to 1.2 µg of was injected per mouse. The PA-Hoc displayed on T4 nanoparticles gave the best antibody titers. The geometric mean endpoint antibody titer for the T4-displayed PA was 450,000 while the mice immunized with PA and aluminum hydroxide as an adjuvant had a geometric mean end point titer of 156,000. Thus, the T4 nanoparticles without any added adjuvant generated about 3-fold greater antibody titers than that with alum as an adjuvant. These data show that the T4 nanoparticles are highly immunogenic and could serve as a valuable platform to test anthrax antigen formulations.

EXAMPLE 11

Cellular Responses

To examine cellular responses to T4 nanoparticles, spleen and lymph node cells were collected four weeks after second boost and single cell preparations were made. Cells were analyzed for T cell proliferative responses by tritiated thymidine (3H-Tdr) incorporation. Cells were incubated with varying concentrations of baculovirus-expressed p24 (closed circles) or with varying concentrations of an irrelevant antigen, ovalbumin (open circles) for 72 hrs. During the last 16 hrs of the culture period, cells were pulsed with 3H-Tdr. Cells were then harvested onto glass fiber filters. The filters were processed and counted in a beta plate counter. The data are expressed as the stimulation index, which represents the ratio of 3H-Tdr in lymphocyte cultures pulsed with the antigen to 3H-Tdr in lymphocyte cultures pulsed with medium alone. A stimulation index of 3 or greater was considered a positive response.

As FIG. 13 shows, the T4 nanoparticles of the present invention elicited strong cellular responses. As with the antibody response, mice immunized with p24 alone did not induce any proliferative responses. In contrast, spleen cells from mice immunized with either p24-Hoc or with Hoc-p24 displayed on T4 induced robust T cell responses in the presence of 1-10 µg baculovirus expressed p24 (FIG. 13). Stimulation indices of 80-100 were obtained at an antigen concentration of 10 µg/ml. Similar proliferative responses were obtained with lymph node cells (data not shown). Naive mice did not induce any p24-specific proliferative T cell responses, thus demonstrating that the responses obtained were specific. In all cases, the negative control antigen, ovalbumin, did not induce any proliferative responses (FIG. 13). Both IL-4 and IFN-gamma were induced only from spleen and lymph node cells of mice immunized with either p24-Hoc-T4 or with Hoc-p24-T4 (data not shown). Chromium release assays demonstrated that spleen cells obtained from p24-Hoc-T4 or with Hoc-p24-T4 immunized mice showed approximately 18-22% antigen-specific lysis (data not shown). Taken together with the examples above, these results show that p24 displayed on phage T4 can induce robust humoral and cell-mediated immune responses and does not require the addition of any external adjuvant to manifest its immunogenicity.

I claim:

1. A method for making an immunogenic T4 bacteriophage composition, comprising the following steps:
   (a) constructing one or more Hoc fusion proteins and one or more Soc fusion proteins;
   (b) isolating Hoc and Soc negative T4 bacteriophage capsids; and
   (c) mixing the Hoc and Soc fusion proteins with the T4 bacteriophage capsids in vitro to thereby bind the Hoc and Soc fusion proteins to the T4 bacteriophage capsids, wherein there are a defined number of Hoc and Soc binding sites on each of the capsids,
   wherein the Hoc and Soc fusion proteins are mixed in step (c) at a selected ratio of the number of molecules of each of the Hoc fusion proteins to the total number of Hoc binding sites and at a selected ratio of the number of molecules of each of the Soc fusion proteins to the total number of Soc binding sites, respectively, so that the copy number of each of the Hoc fusion proteins bound on each capsid after step (c) is controlled and the copy number of each of the Soc fusion proteins bound on each capsid after step (c) is controlled,
   wherein fewer than all of the Hoc binding sites on each of the capsids are bound by the Hoc fusion proteins after step (c), and
   wherein the ratio of the number of molecules of the one or more Hoc fusion proteins to the total number of Hoc binding sites on the T4 bacteriophage capsids mixed in vitro during step (c) is between 1:5 and 1:100.

2. The method of claim 1, wherein the mixing of the Hoc and Soc fusion proteins onto T4 bacteriophage capsids comprises incubation of the Hoc and Soc fusion proteins with the T4 bacteriophage capsids in a reaction buffer.

3. The method of claim 2, wherein the reaction buffer comprises Tris buffered saline, phosphate buffered saline, or hepes buffer.

4. The method of claim 1, wherein each T4 bacteriophage capsid is devoid of DNA.

5. The method of claim 1, wherein each T4 bacteriophage capsid comprises a DNA construct.

6. A method for making an immunogenic T4 bacteriophage composition, comprising the following steps:
   (a) constructing two or more Hoc fusion proteins, each of the Hoc fusion proteins comprising a foreign protein fused to a Hoc protein or fragment thereof;
   (b) isolating Hoc and/or Soc negative T4 bacteriophage capsids; and
   (c) mixing the Hoc fusion proteins with the Hoc and/or Soc negative T4 bacteriophage capsids in vitro to thereby bind the Hoc fusion proteins to the T4 bacteriophage capsids,
   wherein there are a defined number of Hoc binding sites on each of the capsids,
   wherein the Hoc fusion proteins are mixed in step (c) at selected respective ratios of the number of molecules of each of the Hoc fusion proteins to the total number of Hoc binding sites so that the respective copy numbers of each of the Hoc fusion proteins bound on each of the capsids after step (c) is controlled,
   wherein each of the Hoc fusion proteins comprises a different foreign protein,
   wherein fewer than all of the Hoc sites on each of the capsids are bound by the Hoc fusion proteins after step (c), and
   wherein the ratio of the number of molecules of the two or more Hoc fusion proteins to the total number of Hoc binding sites on the T4 bacteriophage capsids mixed in vitro during step (c) is between 1:5 and 1:100.

7. The method of claim 6, wherein step (c) facilitates an interaction between two or more of the foreign proteins.

8. The method of claim 7, wherein the interaction between the two or more of the foreign proteins facilitates the presentation of an antibody binding site.

9. The method of claim 6, wherein one or more of the foreign proteins comprises a mycobacterial antigen and wherein one or more of the foreign proteins comprises a human immunodeficiency viral antigen.

10. The method of claim 6, wherein one or more of the foreign proteins is selected from the group consisting of: interleukins, phospholipase A2, endotoxins, staphylococcal enterotoxin B, type I interferons, type II interferons, tumor necrosis factor alpha (TNF-α), tumor necrosis factor beta (TNF-β), transforming growth factor-β (TGF-β), transforming growth factor alpha (TGF-α), lymphotoxin, macrophage migration inhibition factor (MIF), granulocyte-macrophage colony-stimulating factor (GM-CSF), monocyte-macrophage colony-stimulating factor (M-CSF), granulocyte colony-stimulating factor (G-CSF), vascular epithelial growth factor (VEGF), angiogenin, heat shock proteins (HSPs), fibroblast growth factor (FGF), tumor-associated antigens (TAA), melanoma antigen recognized by T-cells 1 (MART-1), melanoma-associated antigens (MAGE), B melanoma antigen 1 (BAGE), mutant p53, tyrosinase, mucins, MUC-1, prostate specific antigen (PSA), thyroid-stimulating hormone (TSH), autoimmune antigens, angiostatin, endostatin, basic fibroblast growth factor (bFGF), and vascular endothelial growth factor (VEGF).

11. The method of claim 1, further comprising the following step:
(d) binding one or more molecular components to one or more of the Hoc and/or Soc fusion proteins, wherein the molecular component is selected from the group consisting of: lipid A, nucleotides, DNA, RNA, and mRNA.

12. The method of claim 6, further comprising the following step:
(d) binding one or more molecular components to one or more of the Hoc fusion proteins, wherein each of the one or more molecular components is selected from the group consisting of: lipid A, nucleotides, DNA, RNA, and mRNA.

13. The method of claim 1, wherein each Hoc fusion protein comprises a foreign protein fused to a Hoc protein or fragment thereof and wherein each Soc fusion protein comprises a foreign protein fused to a Soc protein or fragment thereof.

14. The method of claim 13, wherein at least one of the Hoc fusion proteins comprises a foreign protein that is antigenic.

15. The method of claim 13, wherein at least one of the Soc fusion proteins comprises a foreign protein that is antigenic.

16. The method of claim 13, wherein the mixing of the Hoc fusion proteins and the Soc fusion proteins onto the T4 bacteriophage capsids in step (c) facilitates an interaction between the foreign protein of one of the Hoc fusion proteins and the foreign protein of one of the Soc fusion proteins.

17. The method of claim 16, wherein the interaction between the foreign protein of one of the Hoc fusion proteins and the foreign protein of one of the Soc fusion proteins facilitates the presentation of an antibody binding site.

18. The method of claim 13, wherein one or more of the foreign proteins comprises a mycobacterial antigen and wherein one or more of the foreign proteins comprises a human immunodeficiency viral antigen.

19. The method of claim 13, wherein each Hoc fusion protein comprises a foreign protein selected from the group consisting of: interleukins, phospholipase A2, endotoxins, staphylococcal enterotoxin B, type I interferons, type II interferons, tumor necrosis factor alpha (TNF-α), tumor necrosis factor beta (TNF-β), transforming growth factor-β (TGF-β), transforming growth factor alpha (TGF-α), lymphotoxin, macrophage migration inhibition factor (MIF), granulocyte-macrophage colony-stimulating factor (GM-CSF), monocyte-macrophage colony-stimulating factor (M-CSF), granulocyte colony-stimulating factor (G-CSF), vascular epithelial growth factor (VEGF), angiogenin, heat shock proteins (HSPs), fibroblast growth factor (FGF), tumor-associated antigens (TAA), melanoma antigen recognized by T-cells 1 (MART-1), melanoma-associated antigens (MAGE), B melanoma antigen 1 (BAGE), mutant p53, tyrosinase, mucins, MUC-1, prostate specific antigen (PSA), thyroid-stimulating hormone (TSH), autoimmune antigens, angiostatin, endostatin, basic fibroblast growth factor (bFGF), and vascular endothelial growth factor (VEGF).

20. The method of claim 13, wherein each Soc fusion protein comprises a foreign protein selected from the group consisting of: interleukins, phospholipase A2, endotoxins, staphylococcal enterotoxin B, type I interferons, type II interferons, tumor necrosis factor alpha (TNF-α), tumor necrosis factor beta (TNF-β), transforming growth factor-β (TGF-β), transforming growth factor alpha (TGF-α), lymphotoxin, macrophage migration inhibition factor (MIF), granulocyte-macrophage colony-stimulating factor (GM-CSF), monocyte-macrophage colony-stimulating factor (M-CSF), granulocyte colony-stimulating factor (G-CSF), vascular epithelial growth factor (VEGF), angiogenin, heat shock proteins (HSPs), fibroblast growth factor (FGF), tumor-associated antigens (TAA), melanoma antigen recognized by T-cells 1 (MART-1), melanoma-associated antigens (MAGE), B melanoma antigen 1 (BAGE), mutant p53, tyrosinase, mucins, MUC-1, prostate specific antigen (PSA), thyroid-stimulating hormone (TSH), autoimmune antigens, angiostatin, endostatin, basic fibroblast growth factor (bFGF), and vascular endothelial growth factor (VEGF).

21. The method of claim 13, wherein at least one of the Hoc fusion proteins comprises a first foreign protein, wherein at least one of the Soc fusions proteins comprises a second foreign protein, and wherein the first foreign protein is a different foreign protein than the second foreign protein.

22. The method of claim 1, wherein step (a) comprises constructing a first Hoc fusion protein and a second Hoc fusion protein, wherein the first Hoc fusion protein comprises a first foreign protein fused to a Hoc protein or fragment thereof, wherein the second Hoc fusion protein comprises a second foreign protein fused to a Hoc protein or fragment thereof, wherein at least one of the Soc fusion proteins comprises a third foreign protein fused to a Soc protein or a fragment thereof, and wherein the first foreign protein, the second foreign protein and the third foreign protein are all different foreign proteins.

23. The method of claim 1, wherein step (a) comprises constructing a first Soc fusion protein and a second Soc fusion protein, wherein the first Soc fusion protein comprises a first foreign protein fused to a Soc protein or fragment thereof, wherein the second Soc fusion protein comprises a second foreign protein fused to a Soc protein or fragment thereof, wherein at least one of the Hoc fusion proteins comprises a third foreign protein fused to a Hoc protein or a fragment thereof, and wherein the first foreign protein, the second foreign protein and the third foreign protein are all different foreign proteins.

24. The method of claim 6,
wherein step (a) further comprises constructing two or more Soc fusion proteins, each of the Soc fusion proteins comprising a foreign protein fused to a Soc protein or a fragment thereof,
wherein step (c) further comprises mixing the two or more Soc fusion proteins with the Soc negative T4 bacteriophage capsids in vitro,
wherein there are a defined number of Soc binding sites on each of the capsids,
wherein the Soc fusion proteins are mixed in step (c) at selected respective ratios of the number of molecules of each of the two or more Soc fusion proteins to the total number of Soc binding sites so that the respective copy numbers of each of the two or more Soc fusion proteins bound on each of the capsids is controlled.

25. The method of claim 24, wherein each of the Hoc fusion proteins and each of the Soc fusions proteins comprises a different foreign protein.

26. The method of claim 1, wherein fewer than all of the Soc binding sites on each of the capsids are bound by the Soc fusion proteins after step (c).

27. The method of claim 24, wherein each of the two or more Soc fusion proteins comprises a different foreign protein.

28. The method of claim 24, wherein fewer than all of the Soc binding sites on each of the capsids are bound by the Soc fusion proteins after step (c).

29. A method for making an immunogenic T4 bacteriophage composition, comprising the following steps:
   (a) constructing one or more Hoc fusion proteins, each Hoc fusion protein comprising a foreign protein fused to a Hoc protein, or a fragment thereof;
   (b) isolating Hoc negative T4 bacteriophage capsids; and
   (c) mixing the Hoc fusion proteins with the T4 bacteriophage capsids in vitro to thereby bind the Hoc fusion proteins to the T4 bacteriophage capsids,
   wherein there are a defined number of Hoc binding sites on each of the capsids,
   wherein the Hoc fusion proteins are mixed in step (c) at a selected ratio of the number of molecules of each of the Hoc fusion proteins to the total number of Hoc binding sites so that the copy number of each of the Hoc fusion proteins bound on each capsid after step (c) is controlled,
   wherein fewer than all of the Hoc binding sites on each of the capsids are bound by the Hoc fusion proteins after step (c), and
   wherein the ratio of the number of molecules of the one or more Hoc fusion proteins to the total number of Hoc binding sites on the T4 bacteriophage capsids mixed in vitro during step (c) is between 1:5 and 1:100.

30. The method of claim 29, wherein each T4 bacteriophage capsid is devoid of DNA.

31. The method of claim 29, wherein each T4 bacteriophage capsid comprises a DNA construct.

32. The method of claim 29, further comprising the following step:
   (d) binding one or more molecular components to one or more of the Hoc fusion proteins, wherein the molecular component is selected from the group consisting of: lipid A, nucleotides, DNA, RNA, and mRNA.

33. The method of claim 29, wherein at least one of the Hoc fusion proteins comprises a foreign protein that is antigenic.

34. The method of claim 29, wherein one or more of the foreign proteins comprises a mycobacterial antigen, and wherein one or more of the foreign proteins comprises a human immunodeficiency viral antigen.

35. The method of claim 29, wherein one or more of the foreign proteins is selected from the group consisting of: interleukins, phospholipase A2, endotoxins, staphylococcal enterotoxin B, type I interferons, type II interferons, tumor necrosis factor alpha (TNF-$\alpha$), tumor necrosis factor beta (TNF-$\beta$), transforming growth factor-$\beta$ (TGF-$\beta$), transforming growth factor alpha (TGF-$\alpha$), lymphotoxin, macrophage migration inhibition factor (MIF), granulocyte-macrophage colony-stimulating factor (GM-CSF), monocyte-macrophage colony-stimulating factor (M-CSF), granulocyte colony-stimulating factor (G-CSF), vascular epithelial growth factor (VEGF), angiogenin, heat shock proteins (HSPs), fibroblast growth factor (FGF), tumor-associated antigens (TAA), melanoma antigen recognized by T-cells 1 (MART-1), melanoma-associated antigens (MAGE), B melanoma antigen 1 (BAGE), mutant p53, tyrosinase, mucins, MUC-1, prostate specific antigen (PSA), thyroid-stimulating hormone (TSH), autoimmune antigens, angiostatin, endostatin, basic fibroblast growth factor (bFGF), and vascular endothelial growth factor (VEGF).

* * * * *